United States Patent
Wang et al.

(10) Patent No.: US 11,352,331 B2
(45) Date of Patent: Jun. 7, 2022

(54) CRYSTAL AND SALT OF 4-(NAPHTHALEN-1-YL)-4H-1,2,4-TRIAZOLE COMPOUND AND PREPARATION METHOD THEREFOR

(71) Applicant: MEDSHINE DISCOVERY INC., Jiangsu (CN)

(72) Inventors: Jianfei Wang, Shanghai (CN); Yang Zhang, Shanghai (CN); Jian Li, Shanghai (CN); Shuhui Chen, Shanghai (CN)

(73) Assignee: MEDSHINE DISCOVERY, Jiangsu (CN)

( * ) Notice: Subject to any disclaimer, the term of this patent is extended or adjusted under 35 U.S.C. 154(b) by 0 days.

(21) Appl. No.: 16/772,300

(22) PCT Filed: Dec. 17, 2018

(86) PCT No.: PCT/CN2018/121477
§ 371 (c)(1),
(2) Date: Jun. 12, 2020

(87) PCT Pub. No.: WO2019/114838
PCT Pub. Date: Jun. 20, 2019

(65) Prior Publication Data
US 2021/0078960 A1 Mar. 18, 2021

(30) Foreign Application Priority Data

Dec. 15, 2017 (CN) .......................... 201711352291.0
Dec. 19, 2017 (CN) .......................... 201711376759.X

(51) Int. Cl.
*C07D 249/12* (2006.01)
*A61P 19/06* (2006.01)

(52) U.S. Cl.
CPC ............ *C07D 249/12* (2013.01); *A61P 19/06* (2018.01); *C07B 2200/13* (2013.01)

(58) Field of Classification Search
CPC .................................................. C07D 249/12
USPC ......................................................... 514/384
See application file for complete search history.

(56) References Cited

U.S. PATENT DOCUMENTS 10,633,351 B2 * 4/2020 Wang .................... C07D 249/10

FOREIGN PATENT DOCUMENTS

| CN | 101918377 A | 12/2010 |
|---|---|---|
| CN | 105985295 A | 10/2016 |
| CN | 106220577 A | 12/2016 |
| CN | 201711352291.0 | 12/2017 |
| CN | 201711376759.X | 12/2017 |
| WO | WO-2009070740 A2 | 6/2009 |
| WO | WO-2016000568 A1 | 1/2016 |
| WO | WO-2017215589 A1 | 12/2017 |

OTHER PUBLICATIONS

Mar. 22, 2019 International Search Report issued in International Patent Application No. PCT/CN2018/121477.
Mar. 22, 2019 Written Opinion of the International Searching Authority issued in International Patent Application No. PCT/CN2018/121477.
Extended European Search Report issued in European Application No. 18888224.5, dated Jul. 2, 2021.
Mino R Caira Ed—Montchamp Jean-Luc: "Crystalline Polymorphism of Organic Compounds", Topics in Current Chemstry, Springer, Berlin, DE, vol. 198, Jan. 1998 (Jan. 1998), pp. 163-208, XP008166276, ISSN: 0340-1022, DOI: 10. 1007/3-540-69178-2_5 [retrieved on Feb. 26, 1999].
Hilfiker, R, Blatter, F. von Raum, M: "Relevance of Solid-state Properties for Pharmaceutical Products"; 1" In: Hilfiker, R.: "Polymorphism in the Pharmaceutical Industry", Jan. 2006 (Jan. 2006), WILEY-VCH, Weinheim, XP002528052, ISBN: 978-3-527-31146-0.

* cited by examiner

Primary Examiner — Niloofar Rahmani
(74) Attorney, Agent, or Firm — Harness, Dickey & Pierce, P.L.C.; Donald G. Walker

(57) ABSTRACT

Disclosed are a crystal of a 4-(naphthalene-1-yl)-4H-1,2,4-triazole compound (1) and a preparation method therefor, also comprised are applications of the crystal in preparing a medicament for treating an abnormal uric acid level-related disease.

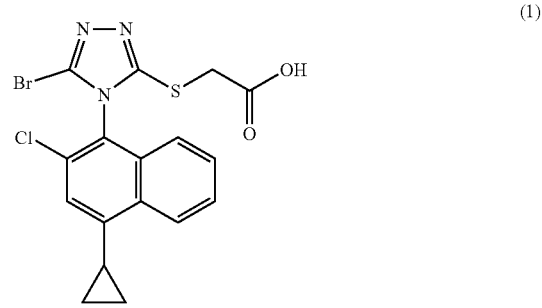

(1)

7 Claims, 11 Drawing Sheets

CRYSTAL AND SALT OF 4-(NAPHTHALEN-1-YL)-4H-1,2,4-TRIAZOLE COMPOUND AND PREPARATION METHOD THEREFOR

CROSS-REFERENCE TO RELATED APPLICATIONS

This application is a 371 National Phase of International Application No. PCT/CN2018/121477, filed Dec. 17, 2018, which claims the benefit of Chinese Patent Application No. CN 201711352291.0, filed Dec. 15, 2017, and Chinese Patent Application No. CN 201711376759.X, filed Dec. 19, 2017. The entire disclosures of the above applications are incorporated herein by reference.

FIELD OF THE INVENTION

The present disclosure relates to a crystal form of 4-(naphthalen-1-yl)-4H-1,2,4-triazol-containing compound and a preparation method thereof, and also involves a use of the crystal form in the preparation of a medicament for the treatment of a disease related to abnormal level of uric acid.

BACKGROUND OF THE INVENTION

In recent years, as people's living habits changes, the onset of hyperuricemia and gout diseases shows an increasing trend year by year. In Europe and the United States, epidemiological studies have shown that gouty arthritis patients account for 1-2% of the total population and gouty arthritis is the main type of arthritis in adult males. Bloomberg estimates that there will be 17.7 million gout patients in 2021. In China, survey shows that, among the population aged 20 to 74, 25.3% of the population have a relatively high level of uric acid in blood, and 0.36% of the population suffer from gout disease. At present, clinical drugs mainly include 1) drugs that inhibit the production of uric acid, such as xanthine oxidase inhibitors allopurinol and febuxostat; 2) drugs that promote the excretion of uric acid, such as probenecid and benzbromarone; 3) inflammation inhibitors, such as colchicine. These drugs have certain drawbacks in the treatment, among which poor efficacy, severe side effects and high cost become the major bottlenecks for clinical applications of these drugs. According to reports, 40%-70% of the patients did not achieve the expected therapeutical goal (<6 mg/dL) after receiving standard therapies.

URAT1 is an important renal anion transporter, which is located on the brush border membrane of epithelial cells of renal tubules, specifically transports uric acid from renal tubules to epithelial cells, and is a major driving force for uric acid reabsorption in renal tubules. Therefore, significant inhibition of the urate transporter URAT1 will increase the excretion of uric acid in the body, thereby reducing the uric acid level in blood and decreasing the possibility of gout attacks.

In December 2015, US FDA approved the first URAT1 inhibitor lesinurad (as shown below) developed by AstraZeneca, and also approved the drug to be used at a dose of 200 mg/day in combination with a xanthine oxidase inhibitor (XOI) (e.g., febuxostat) for the treatment of hyperuricemia and gouty arthritis, but the combination therapy did not produce a significant additional effect compared with the xanthine oxidase inhibitor used alone. Moreover, lesinurad at a dose of 400 mg/day was not approved because of the significantly increased toxic and side effects observed at high doses (relatively high incidence rate of adverse renal events, especially the high incidence rate of nephrolithiasis), although high-dose combination therapies exhibit greater additional effects. Therefore, FDA required a black box warning on the lesinurad label to warn medical staff of the risk of acute renal failure, which occurs more frequently especially when the drug is not used in combination with XOI, and the risk of kidney failure is even higher if lesinurad is used at an over-approved dose. Additionally, FDA required that AstraZeneca continued to investigate lesinurad's renal and cardiovascular safety profile after it was launched to the market. For long-term use in metabolic disease, the safety of drugs is particularly important. Therefore, there is an urgent need for safe uric acid-lowering drugs in this field.

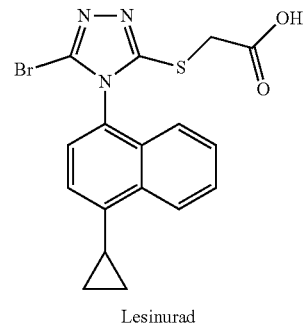 [SMILES: O=C(O)CSc1nnc(Br)n1-c1ccc(C2CC2)c2ccccc12]

Lesinurad

The new drug application report from AstraZeneca has reported in detail the identification results of metabolites of lesinurad by liver microsomes and in liver cells of different genuses of animals in vitro. The data showed that, major metabolites M3 and M4 were detected when lesinurad was metabolized in monkey and human liver cells, but they were not detected when lesinurad was metabolized in dog or rat liver cells, as shown in Table-a below.

TABLE-a

| System | Genus | M3 | M4 | Lesinurad | Total |
| --- | --- | --- | --- | --- | --- |
| Liver microsomes | Rat | — | — | 100 | 100 |
| | Dog | — | — | 100 | 100 |
| | Monkey | 7.9 | — | 92.1 | 100 |
| | Human | — | — | 100 | 100 |
| Liver cells | Rat | — | — | 100 | 100 |
| | Dog | — | — | 100 | 100 |
| | Monkey | 1.45 | 0.47 | 98.1 | 100 |
| | Human | 2.24 | 5.69 | 92.1 | 100 |

Moreover, AstraZeneca also reported the major metabolites and metabolic pathways of lesinurad after administration to various genuses of animals, and the dihydroxy metabolite M4 was specifically detected in human metabolites:

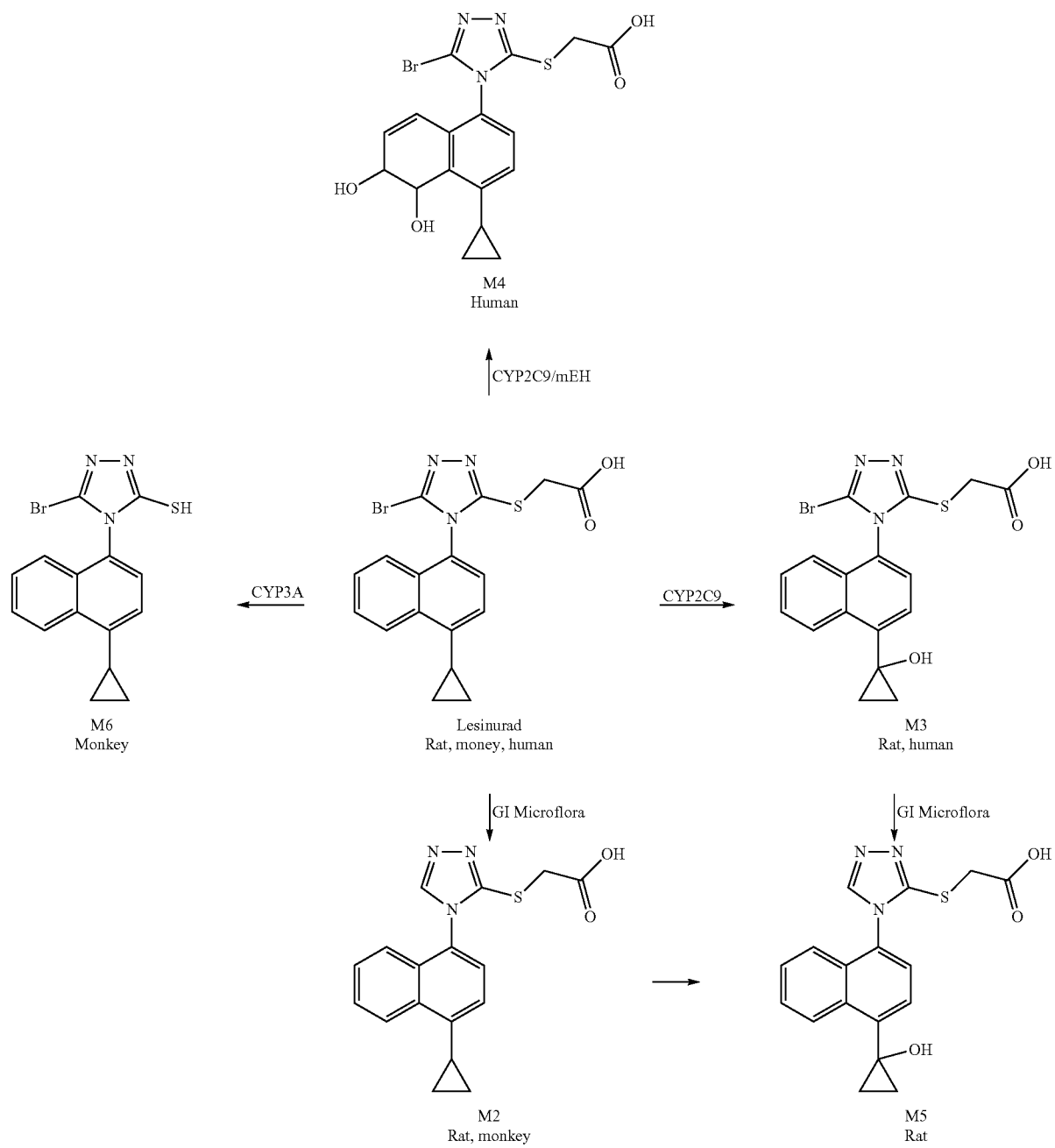
This is consistent with the clinical data of lesinurad in human. Experimental data shows that M3 and M4 are the major metabolites found clinically in human, as shown in Table-b below.
TABLE-b
| System | Time (hour) | Percentage of the administered dose | | | | | | | | | | |
|---|---|---|---|---|---|---|---|---|---|---|---|---|
| | | M1 | M2 | M3 | M3b | M4 | M5 | M5b | M16 | Others | Lesinurad | Total |
| Urine | 0-144 | 1.5 | 0.3 | 12.0 | 1.0 | 15.7 | ND | ND | 0.5 | 1.2 | 31.3 | 63.4 |
| Faeces | 0-144 | ND | 4.8 | 0.3 | 1.9 | 5.0 | 3.6 | 7.8 | 1.1 | 7.5 | 1.5 | 33.5 |

The production of the metabolite M4 is determined as the result of the joint action of cytochrome CYP2C9 and epoxide hydrolase mEH of primates. This mEH metabolic pathway is unique to primate species, which explains why M4 is not observed in rats and dogs.

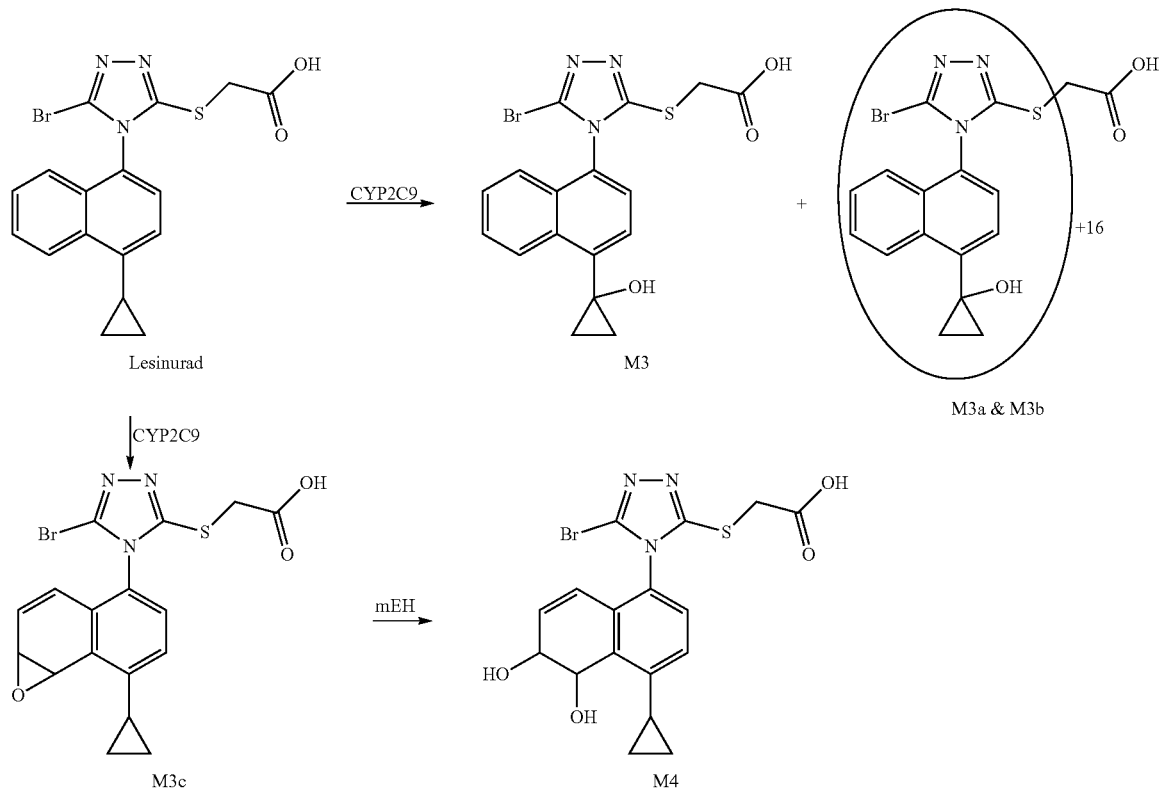

Content of the Invention

The present disclosure provides a crystal form A of compound 1, wherein the X-ray powder diffraction pattern thereof comprises characteristic diffraction peaks at angle 2θ of 7.16±0.2°, 17.98±0.2°, and 22.30±0.2°.

compound 1

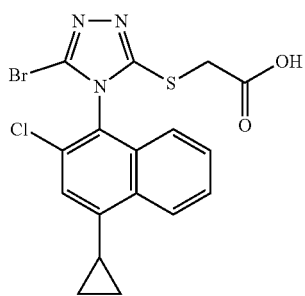

In some embodiments of the present disclosure, the X-ray powder diffraction pattern of the crystal form A of compound 1 comprises characteristic diffraction peaks at angle 2θ of 7.16±0.2°, 12.50±0.2°, 14.61±0.2°, 17.98±0.2°, 19.62±0.2°, 22.30±0.2°, 24.63±0.2°, and 26.37±0.2°.

In some embodiments of the present disclosure, the X-ray powder diffraction pattern of the crystal form A of compound 1 comprises characteristic diffraction peaks at angle 2θ of 7.16±0.2°, 9.56±0.2°, 11.30±0.2°, 12.50±0.2°, 14.61±0.2°, 17.98±0.2°, 18.72±0.2°, 19.62±0.2°, 22.30±0.2°, 24.63±0.2°, and 26.37±0.2°.

In some embodiments of the present disclosure, the XRPD pattern of the crystal form A of compound 1 is as shown in FIG. 1.

In some embodiments of the present disclosure, the analytical data of the XRPD pattern of the crystal form A of compound 1 is as shown in Table 1.

TABLE 1

Analytical data of the XRPD pattern of the crystal form A of compound 1

| No. | 2θ angle (°) | d-spacing (Å) | Intensity (%) |
|---|---|---|---|
| 1 | 7.156 | 12.342 | 69.2 |
| 2 | 9.559 | 9.2446 | 21.5 |
| 3 | 11.302 | 7.8228 | 19.8 |
| 4 | 12.5 | 7.0752 | 68.6 |
| 5 | 12.853 | 6.882 | 19.3 |
| 6 | 14.255 | 6.208 | 11 |
| 7 | 14.614 | 6.0564 | 40.7 |
| 8 | 14.987 | 5.9066 | 9.1 |
| 9 | 16.34 | 5.4202 | 2.7 |
| 10 | 17.983 | 4.9286 | 82.5 |
| 11 | 18.221 | 4.8649 | 14.6 |
| 12 | 18.716 | 4.7373 | 46 |
| 13 | 19.622 | 4.5205 | 32.8 |
| 14 | 20.725 | 4.2822 | 10.7 |

TABLE 1-continued

Analytical data of the XRPD pattern
of the crystal form A of compound 1

| No. | 2θ angle (°) | d-spacing (Å) | Intensity (%) |
|---|---|---|---|
| 15 | 21.1 | 4.2071 | 3 |
| 16 | 22.304 | 3.9825 | 100 |
| 17 | 22.678 | 3.9177 | 22.4 |
| 18 | 23.569 | 3.7715 | 3 |
| 19 | 24.396 | 3.6457 | 37.6 |
| 20 | 24.633 | 3.6111 | 64.2 |
| 21 | 25.065 | 3.5498 | 22.3 |
| 22 | 25.953 | 3.4303 | 13.4 |
| 23 | 26.367 | 3.3774 | 60.7 |
| 24 | 26.644 | 3.3429 | 10 |
| 25 | 27.135 | 3.2835 | 33.1 |
| 26 | 27.513 | 3.2393 | 9.3 |
| 27 | 27.926 | 3.1923 | 10.1 |
| 28 | 28.616 | 3.1169 | 19.5 |
| 29 | 28.912 | 3.0856 | 7.2 |
| 30 | 29.347 | 3.0408 | 2.8 |
| 31 | 30.392 | 2.9387 | 2.7 |
| 32 | 31.02 | 2.8805 | 14.8 |
| 33 | 31.3 | 2.8554 | 31.8 |
| 34 | 32.496 | 2.753 | 3.4 |
| 35 | 33.056 | 2.7076 | 4.8 |
| 36 | 33.232 | 2.6937 | 6.5 |
| 37 | 34.199 | 2.6197 | 2.5 |
| 38 | 34.531 | 2.5953 | 12.9 |
| 39 | 35.852 | 2.5026 | 4.6 |
| 40 | 36.363 | 2.4686 | 5.7 |
| 41 | 37.021 | 2.4263 | 8.5 |
| 42 | 37.557 | 2.3928 | 8.5 |
| 43 | 37.907 | 2.3716 | 4.2 |
| 44 | 38.321 | 2.3469 | 7.9 |
| 45 | 38.975 | 2.309 | 4.3 |
| 46 | 39.306 | 2.2903 | 3.2 |

In some embodiments of the present disclosure, the differential scanning calorimetry curve of the crystal form A of compound 1 has an endothermic peak with an onset at 167.42° C.±2° C.

In some embodiments of the present disclosure, the DSC pattern of the crystal form A of compound 1 is as shown in FIG. 2.

In some embodiments of the present disclosure, the thermogravimetric analysis curve of the crystal form A of compound 1 shows a weight loss of 0.3708% occurred at 143.64° C. 3° C.

In some embodiments of the present disclosure, the TGA pattern of the crystal form A of compound 1 is as shown in FIG. 3.

The present disclosure also provides an amorphous form I of compound 1, wherein the X-ray powder diffraction pattern thereof is as shown in FIG. 4.

In some embodiments of the present disclosure, the DSC pattern of the amorphous form I of compound 1 is as shown in FIG. 5.

In some embodiments of the present disclosure, the thermogravimetric analysis curve of the amorphous form I of compound 1 shows a weight loss of 0.8970% occurred at 116.02±3° C.

In some embodiments of the present disclosure, the TGA pattern of the amorphous form I of compound 1 is as shown in FIG. 6.

The present disclosure also provides a crystal form B of compound 1a, wherein the X-ray powder diffraction pattern thereof comprises characteristic diffraction peaks at angle 2θ of 17.34±0.2°, 20.36±0.2°, and 27.12±0.2°.

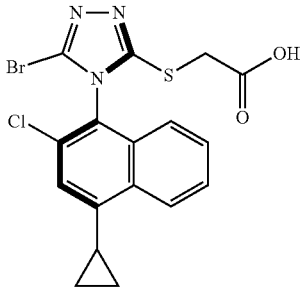

compound 1a

In some embodiments of the present disclosure, the X-ray powder diffraction pattern of the crystal form B of compound 1a comprises characteristic diffraction peaks at angle 2θ of 13.77±0.2°, 15.53±0.2°, 17.34±0.2°, 18.76±0.2°, 20.36±0.2°, 21.31±0.2°, 23.10±0.2°, and 27.12±0.2°.

In some embodiments of the present disclosure, the XRPD pattern of the crystal form B of compound 1a is as shown in FIG. 7.

In some embodiments of the present disclosure, the analytical data of the XRPD pattern of the crystal form B of compound 1a is as shown in Table 2.

TABLE 2

Analytical data of the XRPD pattern
of the crystal form B of compound 1a

| No. | 2θ angle (°) | d-spacing (Å) | Intensity (%) |
|---|---|---|---|
| 1 | 10.697 | 8.2639 | 24.8 |
| 2 | 12.149 | 7.2792 | 26.7 |
| 3 | 13.769 | 6.4259 | 30.9 |
| 4 | 15.529 | 5.7016 | 33.7 |
| 5 | 16.055 | 5.5157 | 25.5 |
| 6 | 17.025 | 5.2037 | 11.6 |
| 7 | 17.338 | 5.1104 | 100 |
| 8 | 18.502 | 4.7914 | 29.1 |
| 9 | 18.761 | 4.726 | 38.9 |
| 10 | 19.902 | 4.4574 | 40.7 |
| 11 | 20.355 | 4.3593 | 70.3 |
| 12 | 20.949 | 4.237 | 32.8 |
| 13 | 21.306 | 4.1667 | 40.2 |
| 14 | 21.736 | 4.0853 | 10.5 |
| 15 | 22.706 | 3.913 | 29.1 |
| 16 | 23.098 | 3.8474 | 33.8 |
| 17 | 23.806 | 3.7346 | 25 |
| 18 | 24.283 | 3.6623 | 10.2 |
| 19 | 25.089 | 3.5465 | 24.5 |
| 20 | 25.623 | 3.4737 | 30.9 |
| 21 | 26.154 | 3.4044 | 17.8 |
| 22 | 26.848 | 3.318 | 10.1 |
| 23 | 27.123 | 3.2849 | 56.2 |
| 24 | 27.38 | 3.2546 | 45.1 |
| 25 | 28.411 | 3.1389 | 10.7 |
| 26 | 29.566 | 3.0188 | 23.9 |
| 27 | 31.225 | 2.8621 | 16.9 |
| 28 | 31.48 | 2.8395 | 8.4 |
| 29 | 32.254 | 2.7731 | 10.2 |
| 30 | 32.615 | 2.7433 | 10.8 |
| 31 | 33.137 | 2.7012 | 17.4 |
| 32 | 33.455 | 2.6762 | 15.4 |
| 33 | 34.283 | 2.6135 | 15.8 |
| 34 | 36.65 | 2.45 | 14.1 |
| 35 | 38.463 | 2.3385 | 8.1 |
| 36 | | | |
| 37 | | | |

In some embodiments of the present disclosure, the differential scanning calorimetry curve of the crystal form B of compound 1a has an endothermic peak with an onset at 140.76° C.±2° C.

In some embodiments of the present disclosure, the DSC pattern of the crystal form B of compound 1a is as shown in FIG. 8.

In some embodiments of the present disclosure, the thermogravimetric analysis curve of the crystal form B of compound 1a shows a weight loss of 0.4590% occurred at 128.08° C.±3° C.

In some embodiments of the present disclosure, the TGA pattern of the crystal form B of compound 1a is as shown in FIG. 9.

The present disclosure also provides an amorphous form II of compound 1a, wherein the X-ray powder diffraction pattern thereof is as shown in FIG. 10.

In some embodiments of the present disclosure, the differential scanning calorimetry curve of the amorphous form II of compound 1a has an exothermic peak with an onset at 91.38° C.±2° C., and an endothermic peak with an onset at 138.32° C.±2° C.

In some embodiments of the present disclosure, the DSC pattern of the amorphous form II of compound 1a is as shown in FIG. 11.

In some embodiments of the present disclosure, the thermogravimetric analysis curve of the amorphous form II of compound 1a shows a weight loss of 1.821% occurred at 101.34° C.±3° C., and a weight loss of 3.629% occurred at 129.17° C.±3° C.

In some embodiments of the present disclosure, the TGA pattern of the amorphous form II of compound 1a is as shown in FIG. 12.

The present disclosure also provides a crystal form C of compound 1b, wherein the X-ray powder diffraction pattern thereof comprises characteristic diffraction peaks at angle 2θ of 17.24±0.2°, 18.68±0.2°, and 20.26±0.2°.

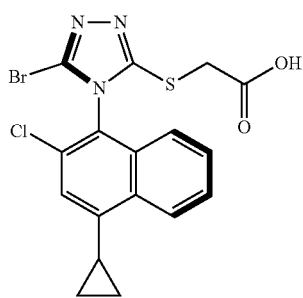

compound 1b

In some embodiments of the present disclosure, the X-ray powder diffraction pattern of the crystal form C of compound 1b comprises characteristic diffraction peaks at angle 2θ of 12.06±0.2°, 13.69±0.2°, 15.46±0.2°, 17.24±0.2°, 18.68±0.2°, 20.26±0.2°, 21.23±0.2°, and 27.04±0.2°.

In some embodiments of the present disclosure, the X-ray powder diffraction pattern of the crystal form C of compound 1b comprises characteristic diffraction peaks at angle 2θ of 10.65±0.2°, 12.06±0.2°, 13.69±0.2°, 15.46±0.2°, 15.97±0.2°, 17.24±0.2°, 18.68±0.2°, 20.26±0.2°, 21.23±0.2°, 23.01±0.2°, and 27.04±0.2°.

In some embodiments of the present disclosure, the XRPD pattern of the crystal form C of compound 1b is as shown in FIG. 13.

In some embodiments of the present disclosure, the analytical data of the XRPD pattern of the crystal form C of compound 1b is as shown in Table 3.

TABLE 3

Analytical data of the XRPD pattern of the crystal form B of compound 1b

| No. | 2θ angle (°) | d-spacing (Å) | Intensity (%) |
|---|---|---|---|
| 1 | 10.652 | 8.2981 | 23.5 |
| 2 | 12.057 | 7.3347 | 30.9 |
| 3 | 13.691 | 6.4625 | 33.9 |
| 4 | 15.463 | 5.7257 | 37 |
| 5 | 15.976 | 5.543 | 25.5 |
| 6 | 16.947 | 5.2274 | 17.6 |
| 7 | 17.245 | 5.1379 | 100 |
| 8 | 18.408 | 4.8159 | 29.8 |
| 9 | 18.681 | 4.7461 | 44.6 |
| 10 | 19.823 | 4.4751 | 44.4 |
| 11 | 20.262 | 4.3792 | 68.4 |
| 12 | 20.869 | 4.253 | 38.1 |
| 13 | 21.228 | 4.182 | 40.1 |
| 14 | 21.644 | 4.1026 | 10.8 |
| 15 | 22.61 | 3.9294 | 27.3 |
| 16 | 23.019 | 3.8604 | 32.8 |
| 17 | 23.519 | 3.7795 | 18.7 |
| 20 | 23.714 | 3.7488 | 25.6 |
| 21 | 24.995 | 3.5596 | 23.6 |
| 22 | 25.53 | 3.4862 | 28.7 |
| 23 | 26.113 | 3.4097 | 15.8 |
| 24 | 26.751 | 3.3297 | 8.1 |
| 25 | 27.044 | 3.2943 | 49.1 |
| 26 | 27.301 | 3.2639 | 39 |
| 27 | 27.496 | 3.2412 | 16.9 |
| 28 | 28.365 | 3.1439 | 7.7 |
| 29 | 29.472 | 3.0283 | 20.2 |
| 30 | 31.132 | 2.8704 | 13.4 |
| 31 | 31.364 | 2.8498 | 9.1 |
| 32 | 32.566 | 2.7473 | 10.6 |
| 33 | 33.043 | 2.7087 | 13 |
| 34 | 33.412 | 2.6796 | 12 |
| 35 | 34.189 | 2.6205 | 15 |
| 36 | 36.587 | 2.454 | 10.8 |

In some embodiments of the present disclosure, the differential scanning calorimetry curve of the crystal form C of compound 1b has an endothermic peak with an onset at 140.13° C.±2° C.

In some embodiments of the present disclosure, the DSC pattern of the crystal form C of compound 1b is as shown in FIG. 14.

In some embodiments of the present disclosure, the thermogravimetric analysis curve of the crystal form C of compound 1b shows a weight loss of 0.6612% occurred at 134.98° C.±3° C.

In some embodiments of the present disclosure, the TGA pattern of the crystal form C of compound 1b is as shown in FIG. 15.

The present disclosure also provides an amorphous form III of compound 1b, wherein the X-ray powder diffraction pattern thereof is as shown in FIG. 16.

In some embodiments of the present disclosure, the differential scanning calorimetry curve of the amorphous form III of compound 1b has an exothermic peak with an onset at 103.05° C.±2° C., and an endothermic peak with an onset at 139.07° C.±2° C.

In some embodiments of the present disclosure, the DSC pattern of the amorphous form III of compound 1b is as shown in FIG. 17.

In some embodiments of the present disclosure, the thermogravimetric analysis curve of the amorphous form III of compound 1b shows a weight loss of 1.035% occurred at 67.14° C.±3° C., a weight loss of 1.647% occurred at 104.04° C.±3° C., and a weight loss of 4.137% occurred at 139.58° C.±3° C.

In some embodiments of the present disclosure, the TGA pattern of the amorphous form III of compound 1b is as shown in FIG. 18.

The present disclosure also provides a crystal form D of compound 1, wherein the X-ray powder diffraction pattern thereof comprises characteristic diffraction peaks at angle 2θ of 9.19±0.2°, 14.41±0.2°, and 19.95±0.2°.

In some embodiments of the present disclosure, the X-ray powder diffraction pattern of the crystal form D of compound 1 comprises characteristic diffraction peaks at angle 2θ of 9.19±0.2°, 10.87±0.2°, 11.63±0.2°, 13.72±0.2°, 14.41±0.2°, 16.90±0.2°, 19.95±0.2°, and 22.22±0.2°.

In some embodiments of the present disclosure, the X-ray powder diffraction pattern of the crystal form D of compound 1 comprises characteristic diffraction peaks at angle 2θ of 9.19±0.2°, 10.87±0.2°, 11.63±0.2°, 13.72±0.2°, 14.41±0.2°, 16.90±0.2°, 19.95±0.2°, 22.22±0.2°, and 26.11±0.2°.

In some embodiments of the present disclosure, the XRPD pattern of the crystal form D of compound 1 is as shown in FIG. 19.

In some embodiments of the present disclosure, the analytical data of the XRPD pattern of the crystal form D of compound 1 is as shown in Table 4.

TABLE 4

| | Analytical data of the XRPD pattern of the crystal form D of compound 1 | | |
|---|---|---|---|
| No. | 2θ angle (°) | d-spacing (Å) | Intensity (%) |
| 1 | 7.200 | 12.2671 | 2.9 |
| 2 | 9.189 | 9.6157 | 34.7 |
| 3 | 10.869 | 8.1332 | 20.3 |
| 4 | 11.628 | 7.6037 | 11.9 |
| 5 | 13.002 | 6.8033 | 2.0 |
| 6 | 13.722 | 6.4478 | 32.0 |
| 7 | 14.414 | 6.1399 | 45.9 |
| 8 | 15.397 | 5.7499 | 10.0 |
| 9 | 15.955 | 5.5503 | 2.8 |
| 10 | 16.901 | 5.2415 | 33.3 |
| 11 | 17.548 | 5.0498 | 4.4 |
| 12 | 18.109 | 4.8945 | 2.3 |
| 13 | 18.38 | 4.823 | 11.7 |
| 14 | 19.069 | 4.6502 | 15.1 |
| 15 | 19.954 | 4.4461 | 100.0 |
| 16 | 21.713 | 4.0895 | 5.0 |
| 17 | 22.225 | 3.9965 | 33.8 |
| 18 | 23.196 | 3.8314 | 4.0 |
| 19 | 23.923 | 3.7166 | 26.4 |
| 20 | 24.476 | 3.6339 | 5.8 |
| 21 | 25.698 | 3.4638 | 14.1 |
| 22 | 25.913 | 3.4355 | 28.7 |
| 23 | 26.111 | 3.4099 | 67.9 |
| 24 | 26.444 | 3.3677 | 15.5 |
| 25 | 27.156 | 3.2810 | 4.5 |
| 26 | 27.416 | 3.2505 | 18.6 |
| 27 | 27.689 | 3.2190 | 16.2 |
| 28 | 27.963 | 3.1881 | 27.6 |
| 29 | 28.615 | 3.1170 | 3.9 |
| 30 | 29.172 | 3.0587 | 3.6 |
| 31 | 29.801 | 2.9955 | 8.9 |
| 32 | 30.274 | 2.9498 | 5.5 |
| 33 | 31.360 | 2.8501 | 6.4 |
| 34 | 31.513 | 2.8366 | 12.3 |
| 35 | 33.332 | 2.6859 | 4.1 |
| 36 | 34.102 | 2.6269 | 9.8 |
| 37 | 34.769 | 2.578 | 4.2 |
| 38 | 35.300 | 2.5405 | 7.3 |
| 39 | 36.621 | 2.4518 | 5.1 |
| 40 | 36.939 | 2.4314 | 5.6 |
| 41 | 37.903 | 2.3718 | 3.4 |
| 42 | 38.648 | 2.3278 | 1.9 |
| 43 | 38.974 | 2.3091 | 6.2 |
| 44 | 39.659 | 2.2707 | 2.2 |

In some embodiments of the present disclosure, the differential scanning calorimetry curve of the crystal form D of compound 1 has an endothermic peak with an onset at 183.17° C.±2° C.

In some embodiments of the present disclosure, the DSC pattern of the crystal form D of compound 1 is as shown in FIG. 20.

In some embodiments of the present disclosure, the thermogravimetric analysis curve of the crystal form D of compound 1 shows a weight loss of 0.2658% occurred at 130.95° C. 3° C.

In some embodiments of the present disclosure, the TGA pattern of the crystal form D of compound 1 is as shown in FIG. 21.

The present disclosure also provides a use of the crystal form A of compound 1, the crystal form D of compound 1, the amorphous form I of compound 1, the crystal form B of compound 1a, the amorphous form II of compound 1a, the crystal form C of compound 1b, the amorphous form III of compound 1b in the preparation of a medicament for the treatment of a condition related to abnormal level of uric acid.

In some embodiments of the present disclosure, the condition described above is hyperuricemia, gouty arthritis, nephrolithiasis, urinary calculus, or hypertension.

Technical Effect

Compound 1 (crystal form A), compound 1a (crystal form B), compound 1b (crystal form C) are all stable crystal forms of the compounds which exhibit relatively good stability. Moreover, compound 1a (crystal form B), compound 1b (crystal form C), compound 1 (crystal form A) and (±)-lesinurad exhibit different pharmacokinetic behaviors in cynomolgus monkeys. When administered through PO at a same dose, compared with (±)-lesinurad, compound 1a (crystal form B), compound 1b (crystal form C), and compound 1 (crystal form A) exhibit higher plasma exposure and better overall pharmacokinetic behavior. Compared with (±)-lesinurad, compound 1a (crystal form B) and compound 1 (crystal form A) also exhibit a higher effective coverage rate of the target by the concentration of the compounds in urine (0-24 h).

Definitions and Explanations

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known to those skilled in the art. Preferred embodiments include, but are not limited to, the embodiments of the present disclosure.

The chemical reactions in the embodiments of the present disclosure are carried out in a suitable chemical solvent, and the solvent should be suitable for the chemical change together with the reagents and materials required in the present disclosure. In order to obtain the compounds of the present disclosure, it is sometimes necessary for those skilled in the art to modify or select the synthetic steps or reaction schemes based on the existing embodiments.

The present disclosure will be specifically described below through embodiments, but the scope of the present disclosure is not limited thereto.

All solvents used in the present disclosure are commercially available and can be directly used without further purification.

The present disclosure employs the following abbreviations: DMF represents dimethylformamide; MsOH represents methanesulfonic acid; EtOH represents ethanol; NaOH represents sodium hydroxide.

Compounds are named manually or by ChemDraw® software, and the commercially available compounds employ their vendor directory names.

X-Ray Powder Diffraction Analysis (X-Ray Powder Diffractometer, XRPD) in the Present Disclosure Instrument model: Bruker D8 advance X-ray diffractometer Detection method: about 10-20 mg of the samples was used for XRPD analysis.

Detailed XRPD parameters are as follows:
X-ray tube: Cu, kα, (λ, =1.54056Å).
X-ray tube voltage: 40 kV, X-ray tube current: 40 mA
Divergence slit: 0.60 mm
Detector slit: 10.50 mm
Anti-scattering slit: 7.10 mm
Scanning range: 4-40 deg
Step size: 0.02 deg
Step time: 0.12 seconds
Rotation speed of sample tray: 15 rpm Differential Scanning Calorimetry Analysis (Differential Scanning Calorimeter, DSC) in the Present Disclosure Instrument Model: TA Q2000 differential scanning calorimeter Detection method: samples (about 1 mg) were placed in a DSC aluminum crucible for analysis, and heated from 25° C. to 350° C. with a heating rate of 10° C./min.

Thermogravimetric Analysis (Thermal Gravimetric Analyzer, TGA) in the Present Dislcosure Instrument Model: TA Q5000IR thermal gravimetric analyzer Detection method: samples (2 mg to 5 mg) were placed in a TGA platinum crucible for analysis, and heated from room temperature to 350° C. with a heating rate of 10° C./min.

BRIEF DESCRIPTION OF THE DRAWINGS

FIG. 8 is the DSC pattern of the crystal form B of compound 1a.

FIG. 9 is the TGA pattern of the crystal form B of compound 1a.

FIG. 11 is the DSC pattern of the amorphous form II of compound 1a.

FIG. 12 is the TGA pattern of the amorphous form II of compound 1a.

DETAILED DESCRIPTION OF THE PREFERRED EMBODIMENT

Figure 1:
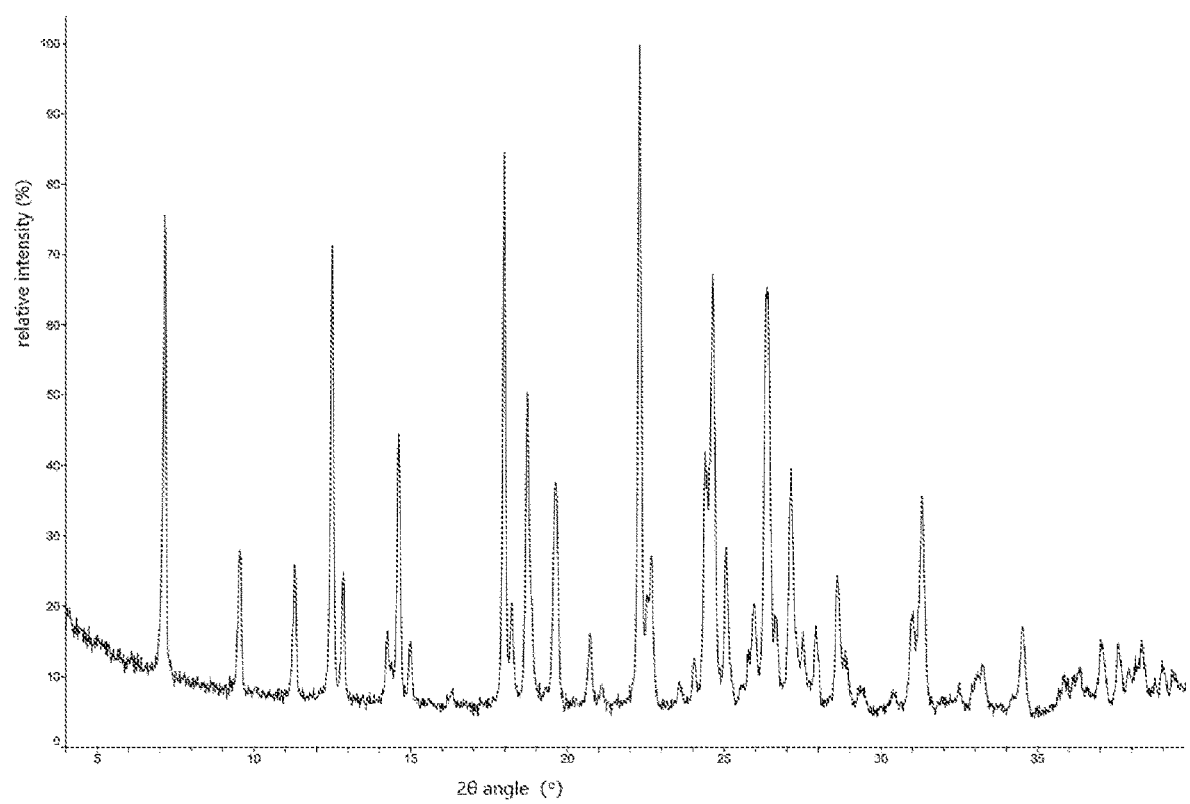
FIG. 1 is the XRPD pattern of the crystal form A of compound 1 measured by Cu-Kα radiation.

In order to better understand the content of the present disclosure, the following embodiments further illustrate the present disclosure, but the present disclosure is not limited thereto.

Embodiment 1: Preparation of Compound 1a ((−)-WX001) and Compound 1b ((+)-WX002)

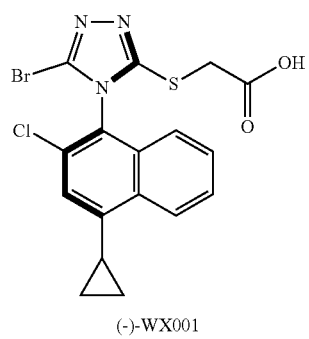

(−)-WX001

Synthesis Route:
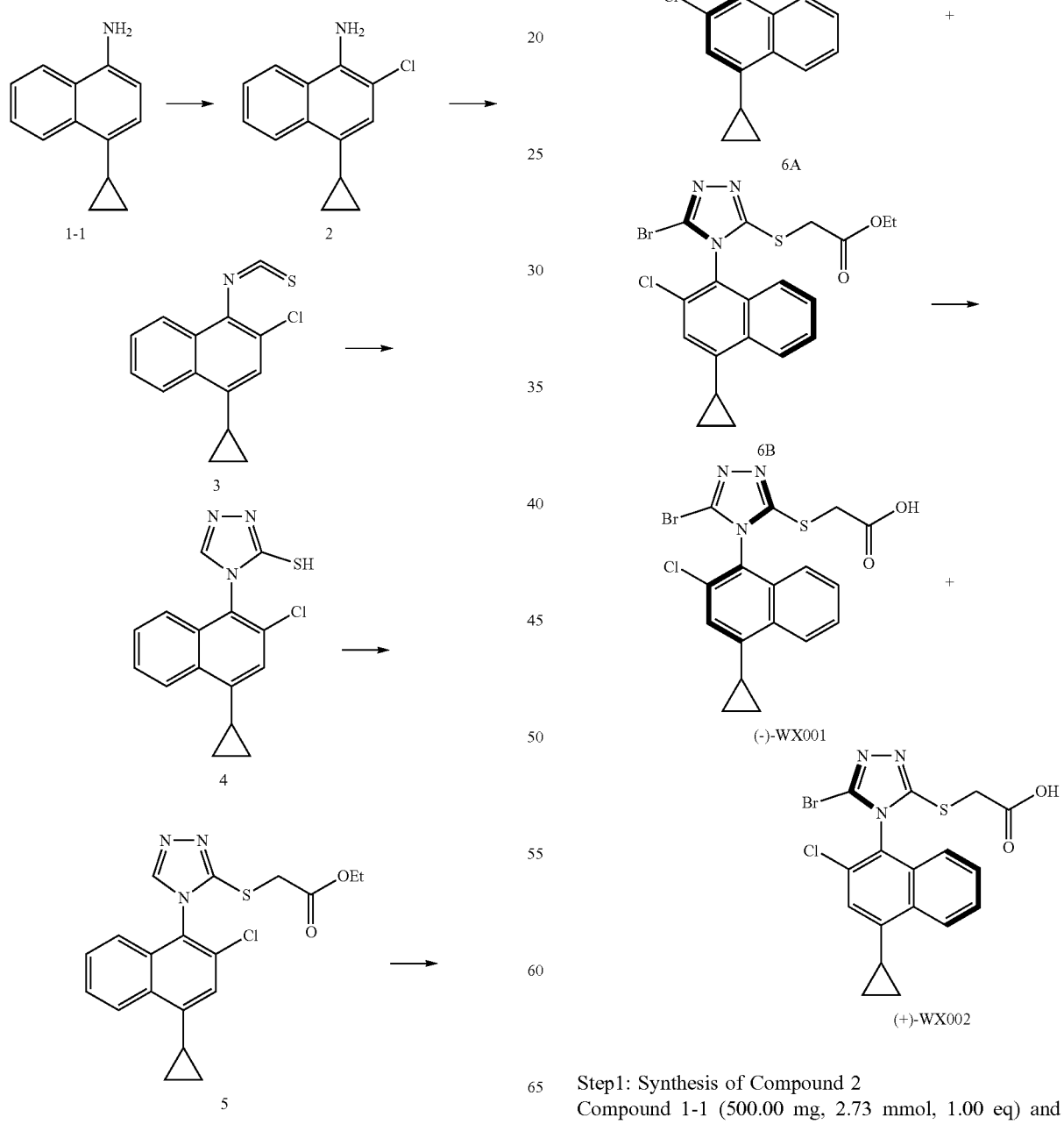
Step 1: Synthesis of Compound 2
Compound 1-1 (500.00 mg, 2.73 mmol, 1.00 eq) and N-chlorosuccinimide (364.34 mg, 2.73 mmol, 1.00 eq) were added into acetic acid (5.00 mL), and the resulting mixture was stirred at 20° C. for 16 hours. After completion of the reaction, the reaction mixture was concentrated directly to remove acetic acid, treated with silica gel (1.0 g), and then purified by automated flash column chromatography (EtOAc/PE=0-10%) to obtain compound 2 as a brown solid (383.00 mg, 1.76 mmol, yield: 64.47%), $^1$H NMR (400 MHz, CDCl$_3$) δ: 8.41-8.35 (m, 1H), 7.85-7.80 (m, 1H), 7.57-7.52 (m, 2H), 7.19 (d, J=0.8 Hz, 1H), 4.43 (s, 2H), 2.26-2.17 (m, 1H), 1.07-0.97 (m, 2H), 0.74-0.67 (m, 2H).

Step2: Synthesis of Compound 3

Compound 2 (360.00 mg, 1.65 mmol, 1.00 eq) and triethylamine (502.02 mg, 4.96 mmol, 687.70 μL, 3.00 eq) were dissolved in dichloromethane (5.00 mL) and cooled to 0° C., followed by dropwise addition of thiophosgene (228.17 mg, 1.98 mmol, 152.12 μL, 1.20 eq). The reaction mixture was stirred at 0° C. for 0.5 hour. Then dilute hydrochloric acid (1 mol/L, 20 mL) was added to quench the reaction, and the resulting mixture was extracted with dichloromethane (10 mL×3). The organic phases were combined, washed with saturated brine (30 mL), dried over anhydrous sodium sulfate and filtered. The filtrate was concentrated to obtain compound 3 as a black liquid (520.00 mg, crude product), which was directly used in the next step.

Step 3: Synthesis of Compound 4

The obtained crude product of compound 3 (520.00 mg, 2.00 mmol, 1.00 eq), hydrazine hydrate (100.12 mg, 2.00 mmol, 97.20 μL, 1.00 eq) and N,N-dimethylformamide dimethyl acetal (285.98 mg, 2.40 mmol, 317.76 μL, 1.20 eq) were added into N,N-dimethylformamide (5.00 mL), and the resulting mixture was stirred at 20° C. for 16 hours. The reaction mixture was concentrated to remove N,N-dimethylformamide. The residue was dissolved in ethyl acetate (20 mL), treated with silica gel (2 g) and then purified by automated flash column chromatography (EtOAc/PE=0-35%) to obtain compound 4 as a white solid (813.00 mg, crude product). $^1$H NMR (400 MHz, Methanol-d$_4$) δ: 8.58 (d, J=8.0 Hz, 1H), 8.37 (s, 1H), 7.73-7.67 (m, 1H), 7.67-7.62 (m, 1H), 7.48-7.45 (m, 1H), 7.38-7.34 (m, 1H), 2.59-2.49 (m, 1H), 1.25-1.18 (m, 2H), 0.96-0.84 (m, 2H).

Step4: Synthesis of Compound 5

The compound 4 (813.00 mg, 2.69 mmol, 1.00 eq), 2-bromoethyl acetate (539.86 mg, 3.23 mmol, 357.53 μL, 1.20 eq) and cesium carbonate (1.76 g, 5.39 mmol, 2.00 eq) were added to N,N-dimethylformamide (5.00 mL), and the resulting mixture was stirred at 20° C. for 16 hours. After completion of the reaction, the reaction mixture was concentrated by an oil pump to give a mixture of yellow oil and white solid, to which acetonitrile (20 mL) was added. The resulting mixture was stirred for 2 minutes and filtered. The filter cake was rinsed with acetonitrile (20 mL), and the filtrates were combined and concentrated to obtain a crude product of compound 5 (1.10 g, crude product) as a yellowish brown oil. $^1$H NMR (400 MHz, CDCl$_3$) δ: 8.49 (d, J=8.4 Hz, 1H), 8.24 (s, 1H), 7.68-7.63 (m, 1H), 7.62-7.59 (m, 1H), 7.39-7.37 (m, 1H), 7.22 (d, J=8.0 Hz, 1H), 4.19-4.17 (m, 2H), 4.16-4.15 (m, 2H), 2.46-2.39 (m, 1H), 1.22-13.18 (m, 2H), 1.06 (t, J=7.2 Hz, 3H), 0.90-0.85 (m, 2H). MS m/z: 388.0 [M+H]$^+$.

Step 5: Synthesis of Compound 6

The crude product of compound 5 (1.10 g, crude product) and N-bromosuccinimide (505.46 mg, 2.84 mmol, 1.00 eq) were added into acetonitrile (10.00 mL), and the resulting mixture was stirred at 18° C. for 2 hours. After completion of the reaction, the reaction mixture was concentrated and purified by automated flash column chromatography (EtOAc/PE=0-25%) to obtain a crude product as a brown oil. The crude product was purified by preparative HPLC to obtain compound 6 as a white solid (201.1 mg, 430.82 μmol). $^1$H NMR (400 MHz, Methanol-d$_4$) δ: 8.64 (d, J=8.0 Hz, 1H), 7.79-7.74 (m, 1H), 7.74-7.69 (m, 1H), 7.52 (d, J=0.8 Hz, 1H), 7.27-7.22 (m, 1H), 4.17-4.09 (m, 2H), 4.08-3.96 (m, 2H), 2.63-2.52 (m, 1H), 1.28-1.23 (m, 5H), 0.97-0.90 (m, 2H). MS m/z: 468.0 [M+H+2]$^+$.

Step 6: Synthesis of Compounds 6A&6B

The compound 6 (201.1 mg, 430.82 μmol, 1.00 eq) was subjected to supercritical fluid chromatography SFC (chiral column: Chiralpak AD (250 mm×30 mm, 5 μm); mobile phase: supercritical CO$_2$/ethanol (0.1% ammonium hydroxide)=30%, 30 min; flow rate: 60 mL/min; detection wavelength: 220 nm) to obtain compound 6A as a transparent oil (50.30 mg, 107.76 μmol) and compound 6B as a transparent oil (52.60 mg, 112.69 μmol).

Compound 6A: SFC (chiral column: Chiralpak AD-3 (100 mm×4.6 mm, 3 μm); mobile phase: ethanol (0.05% diethylamine)/supercritical CO$_2$=5-40%, 4.5 min; 40%, 2.5 min; 5%, 1 min; flow rate: 2.8 mL/min; detection wavelength: 220 nm; column temperature: 40° C.) R$_f$=3.513 min. The excess of this axially chiral isomer was 99.69%.

Compound 6B: SFC (chiral column: Chiralpak AD-3 (100 mm×4.6 mm, 3 μm); mobile phase: ethanol (0.05% diethylamine)/supercritical CO$_2$=5-40%, 4.5 min; 40%, 2.5 min; 5%, 1 min; flow rate: 2.8 mL/min; detection wavelength: 220 nm; column temperature: 40° C.) R$_f$=3.911 min. The excess of this axially chiral isomer was 99.87%.

Step7: Synthesis of Compound (−)-WX001 & (+)-WX002

Compound 6A (50.00 mg, 107.12 μmol, 1.00 eq) and lithium hydroxide monohydrate (22.47 mg, 535.60 μmol, 5.00 eq) were added to ethanol (2.00 mL)/water (2.00 mL), and the resulting mixture was stirred at 20° C. for 16 hours. The reaction mixture was concentrated to remove ethanol, and the pH value of the residual aqueous phase was adjusted to 2 with dilute hydrochloric acid (2 mol/L), during which a white solid precipitated out. The mixture was filtered, and the filter cake was rinsed with water (5 mL). The filter cake was dissolved in ethanol (1 mL), followed by addition of water (20 mL). The mixture was lyophilized to obtain (−)-WX001, which was the amorphous form II of compound 1a (36.30 mg, 82.74 μmol, yield: 77.24%). $^1$H NMR (400 MHz, Methanol-d$_4$) δ: 8.52 (d, J=8.4 Hz, 1H), 7.67-7.55 (m, 2H), 7.39 (s, 1H), 7.13 (d, J=8.0 Hz, 1H), 4.56 (s, 1H), 3.95-3.79 (m, 2H), 2.53-2.39 (m, 1H), 1.18-1.10 (m, 2H), 0.85-0.76 (m, 2H). MS m/z: 439.9 [M+H+2]$^+$. SFC (chiral column: Chiralpak AS-3 (150 mm×4.6 mm, 3 μm); mobile phase: methanol (0.05% diethylamine)/supercritical CO$_2$=5-40%, 5 min; 40%, 2.5 min; 5%, 2.5 min; flow rate: 2.5 mL/min; detection wavelength: 220 nm; column temperature: 35° C.) R$_f$=3.548 min. The excess of this axially chiral isomer was 100%. $[α]^{25}_D$=−0.350 (c=5.0 mg/mL in methanol).

Compound 6B (52.00 mg, 111.40 μmol, 1.00 eq) and lithium hydroxide monohydrate (23.37 mg, 557.00 μmol, 5.00 eq) were added to ethanol (2.00 mL)/water (2.00 mL), and the resulting mixture was stirred at 20° C. for 16 hours. The reaction mixture was concentrated to remove ethanol, and the pH value of the residual aqueous phase was adjusted to 2 with dilute hydrochloric acid (2 mol/L), during which a white solid precipitated out. The mixture was filtered, and the filter cake was rinsed with water (5 mL). The filter cake was dissolved in ethanol (1 mL), followed by addition of water (20 mL). The mixture was lyophilized to obtain (+)-WX002, which was the amorphous form III of compound 1b (36.80 mg, 83.88 μmol, yield: 75.29%). $^1$H NMR (400 MHz, Methanol-$d_4$) δ: 8.64 (d, J=8.4 Hz, 1H), 7.81-7.67 (m, 2H), 7.51 (s, 1H), 7.26 (d, J=8.0 Hz, 1H), 4.14-3.93 (m, 2H), 2.63-2.53 (m, 1H), 1.30-1.23 (m, 2H), 0.97-0.90 (m, 2H). MS m/z: 439.9 [M+H+2]$^+$. SFC (chiral column: Chiralpak AS-3 (150 mm×4.6 mm, 3 μm); mobile phase: methanol (0.05% diethylamine)/supercritical $CO_2$=5-40%, 5 min; 40%, 2.5 min; 5%, 2.5 min; flow rate: 2.5 mL/min; detection wavelength: 220 nm; column temperature: 35° C.) $R_t$=3.774 min. The excess of this axially chiral isomer was 99.22%. $[α]^{25}{}_D$=+1.191 (c=4.6 mg/mL in methanol).

Embodiment 2: Preparation of Compound 1 ((±)-WX003)

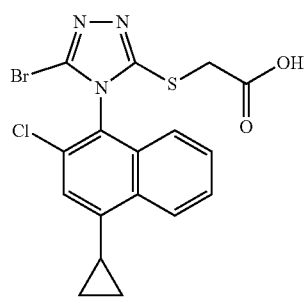

Compound 1

Synthesis Route:

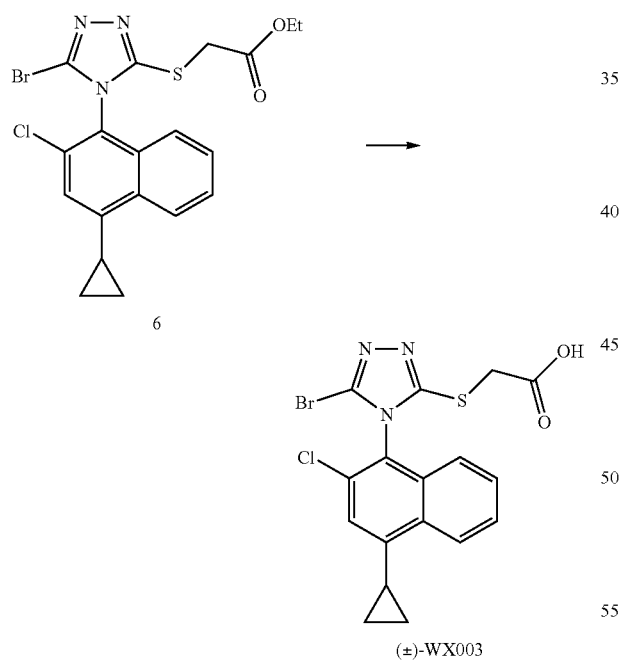

Step1: Synthesis of Compound 1 ((±)-WX003)

Compound 6 (56.30 mg, 120.61 μmol, 1.00 eq) and lithium hydroxide monohydrate (25.30 mg, 603.07 μmol, 5.00 eq) were added to ethanol (2.00 mL)/water (2.00 mL). The reaction was stirred at 20° C. for 16 hours. After completion of the reaction, the reaction mixture was concentrated to remove ethanol, and water was added to obtain a mixture with a final volume of 2 mL. The pH value of the mixture was adjusted to 3 with dilute hydrochloric acid (2 mol/L), during which a white solid precipitated out. The mixture was filtered, and the filter cake was rinsed with water (10 mL) and then dissolved in methanol (1 mL). Subsequently, water (20 mL) was added into the methanol solution, and the resulting mixture was white without precipitated solid. The mixture was lyophilized to obtain compound (±)-WX003 as white powder, which was the amorphous form I of compound 1 (50.30 mg, 114.65 μmol, yield: 91.43%). $^1$H NMR (400 MHz, Methanol-$d_4$) δ: 8.64 (d, J=8.4 Hz, 1H), 7.80-7.67 (m, 2H), 7.52 (s, 1H), 7.26 (br d, J=8.4 Hz, 1H), 4.13-3.95 (m, 2H), 2.63-2.53 (m, 1H), 1.30-1.23 (m, 2H), 0.98-0.90 (m, 2H). MS m/z: 439.6 [M+H]$^+$ Embodiment 3: Preparation of the Crystal Form B of Compound 1a 50 mg of the amorphous form II of compound 1a was added into 0.2 mL of a mixed solvent of ethanol and water (ethanol:water=1:1) or 0.2 mL of a mixed solvent of methanol and water (methanol:water=1:1), and the resulting mixture was stirred to form a suspension. The suspension was placed on a thermostatic homogenizer (40° C.) and shaken for 2 days (protected from light). The residual solid was isolated by centrifugation and dried in a vacuum oven at 30° C. overnight. The obtained solid was tested for crystal form by XRPD, and confirmed to be the crystal form B of compound 1a.

Embodiment 4: Preparation of Crystal Forms of Compound 1a in Different Solvents

The amorphous form II of compound 1a in an appropriate amount were taken in multiple portions, and 0.2 mL of a single or mixed solvent shown in the table below was added respectively. The resulting mixture was stirred at 40° C. After stirring for 2 days, if the sample was in a solution state, the solvent was removed by natural evaporation; if the sample was still in a suspension state, the sample was centrifuged. Solids in all of the samples were collected and tested for crystal form by XRPD. The results are shown in Table 4.

TABLE 4

Preparation of crystal forms of compound 1a in different solvents

| No. | Solvent | Appearance (after 2 days) | Result |
|---|---|---|---|
| 1 | Methanol | A solid precipitated out after the solvent naturally evaporated | Amorphous form II |
| 2 | Ethanol | A solid precipitated out after the solvent naturally evaporated | Amorphous form II |
| 3 | Acetone | A solid precipitated out after the solvent naturally evaporated | Amorphous form II |
| 4 | Acetonitrile | Suspension | Crystal form B |
| 5 | Ethyl acetate | Suspension | Crystal form B |
| 6 | Tetrahydrofuran | A solid precipitated out after the solvent naturally evaporated | Amorphous form II |
| 7 | Water | Suspension | Crystal form B |
| 8 | Methanol:water = 1:1 | Suspension | Crystal form B |

TABLE 4-continued

Preparation of crystal forms of compound 1a in different solvents

| No. | Solvent | Appearance (after 2 days) | Result |
|---|---|---|---|
| 9 | Ethanol:water = 1:1 | Suspension | Crystal form B |
| 10 | Acetone:water = 1:2 | Suspension | Crystal form B |

Embodiment 5: Preparation of the Crystal Form C of Compound 1b 50 mg of the amorphous form III of compound 1b was added to 0.2 mL of a mixed solvent of ethanol and water (ethanol:water=1:1) or 0.2 mL of a mixed solvent of methanol and water (methanol:water=1:1), and the resulting mixture was stirred to form a suspension. The suspension was placed on a thermostatic homogenizer (40° C.) and shaken for 2 days (protected from light). The residual solid was isolated by centrifugation and dried in a vacuum oven at 30° C. overnight. The obtained solid was tested for crystal form by XRPD, and confirmed to be the crystal form C of compound 1b.

Embodiment 6: Preparation of Crystal Forms of Compound 1b in Different Solvents

The amorphous form III of Compound 1b in an appropriate amount were taken in multiple portions, and 0.2 mL of a single or mixed solvent shown in the table below was added respectively. The resulting mixture was stirred at 40° C. After stirring for 2 days, if the sample was in a solution state, the solvent was removed by natural evaporation; if the sample was still in a suspension state, the sample was centrifuged. Solids in all of the samples were collected and tested for crystal form by XRPD. The results are shown in Table 5.

TABLE 5

Preparation of crystal forms of compound 1b in different solvents

| No. | Solvent | Appearance (after 2 days) | Result |
|---|---|---|---|
| 1 | Methanol | A solid precipitated out after the solvent naturally evaporated | Amorphous form III |
| 2 | Ethanol | A solid precipitated out after the solvent naturally evaporated | Amorphous form III |
| 3 | Acetone | A solid precipitated out after the solvent naturally evaporated | Amorphous form III |
| 4 | Acetonitrile | Suspension | Crystal form C |
| 5 | Ethyl acetate | Suspension | Crystal form C |
| 6 | Tetrahydrofuran | A solid precipitated out after the solvent naturally evaporated | Amorphous form III |
| 7 | Water | Suspension | Crystal form C |
| 8 | Methanol:water = 1:1 | Suspension | Crystal form C |
| 9 | Ethanol:water = 1:1 | Suspension | Crystal form C |
| 10 | Acetone:water = 1:2 | Suspension | Crystal form C |

Embodiment 7: Preparation of the Crystal Form a of Compound 1

100 mg of the amorphous form I of compound 1 was added into a glass bottle, followed by addition of ethanol/water (1:1, 1 mL), and the resulting mixture was stirred to form a suspension. The suspension was placed on a thermostatic homogenizer (40° C.) and shaken for 20 hours, and then filtered to collect the sample, which was dried in a vacuum oven at 40° C. overnight. The sample was tested for crystal form by XRPD, and confirmed to be the crystal form A of compound 1.

Embodiment 8: Preparation of Crystal Forms of Compound 1 in Different Solvents

The amorphous form I of compound 1 in an appropriate amount were taken in multiple portions, and 1.0 mL of a single or mixed solvent shown in the table below was added respectively. The resulting mixture was stirred at 40° C. After stirring for 1 day, if the sample was in a solution state, the solvent was removed by natural evaporation; if the sample was still in a suspension state, the sample was centrifuged. Solids in all of the samples were collected and tested for crystal form by XRPD. The results are shown in Table 6.

TABLE 6

Preparation of the crystal forms of compound 1 in different solvents

| No. | Solvent | Appearance (after 1 day) | Result |
|---|---|---|---|
| 2 | Methanol | The sample became a gel after the solvent naturally evaporated | Amorphous form I |
| 3 | Ethanol | A solid precipitated our after the solvent naturally evaporated | Crystal form A |
| 4 | Acetone | The sample became a gel after the solvent naturally evaporated | Amorphous form I |
| 5 | Acetonitrile | Suspension | Crystal form A |
| 6 | Ethyl acetate | Suspension | Crystal form A |
| 7 | Tetrahydrofuran | A solid precipitated our after the solvent naturally evaporated | Crystal form A |
| 8 | Water | Suspension | Crystal form A |
| 9 | Methyl tert-butyl ether | Suspension | Crystal form A |
| 10 | Isopropanol | Suspension | Crystal form A |
| 11 | n-Heptane | Suspension | Crystal form A |
| 12 | Toluene | Suspension | Crystal form A |
| 13 | 2-Tetrahydrofuran | A solid precipitated our after the solvent naturally evaporated | Crystal form A |
| 14 | Methanol:water = 1:1 | Suspension | Crystal form A |
| 15 | Ethanol:water = 1:1 | Suspension | Crystal form A |
| 16 | Acetone:water = 1:2 | Suspension | Crystal form A |
| 17 | Isopropanol:water = 1:1 | Suspension | Crystal form A |
| 18 | Tetrahydrofuran:water = 1:1 | The sample became a gel after the solvent naturally evaporated | Amorphous form I |
| 19 | Toluene:water = 1:1 | Suspension | Crystal form A |

Embodiment 8: Preparation of the Crystal Form D of Compound 1

53 g of the amorphous form I of compound 1 was added into a glass bottle, followed by addition of ethanol/water (1:1, 350 mL), and the resulting mixture was stirred to form a suspension. The suspension was placed on a thermostatic homogenizer (40° C.) and shaken for 48 hours, and then filtered to collect the sample, which was dried in a vacuum oven at 40° C. overnight. The sample was tested for crystal form by XRPD, and confirmed to be the crystal form D of compound 1.

Embodiment 9: Solid Stability Test of the Crystal Form a of Compound 1

According to the "Guidelines for the Stability Test of APIs and Preparations" (Chinese Pharmacopoeia 2015 Edition Part IV general rules 9001), the stability of the crystal form A of compound 1 was investigated at high temperature (60° C., open), high humidity (room temperature/relative humidity 92.5%, open) and strong light (5000 lx, closed).

15 mg of the crystal form A of compound 1 was weighted and placed on the bottom of a glass vial to form a thin layer. Samples placed under high temperature and high humidity conditions were sealed with aluminum foil paper and small holes were punched in the aluminum foil paper to ensure that the sample could fully contact with ambient air; samples placed under strong light conditions were sealed with threaded caps. The samples placed under different conditions were sampled and tested on the 5th day and 10th day (XRPD and HPLC), and the test results were compared with the initial test results obtained on day 0. The results are shown in Table 7 below:

TABLE 7

Solid stability test of the crystal form A of compound 1

| Test condition | Time point | Crystal form |
| --- | --- | --- |
| — | Day 0 | Crystal form A |
| High temperature (60° C., open) | 5th day | Crystal form A |
|  | 10th day | Crystal form A |
| High humidity (room temperature/relative humidity 92.5%, open) | 5th day | Crystal form A |
|  | 10th day | Crystal form A |
| Strong light (5000 lx, closed) | 10th day | Crystal form A |

Conclusion: The crystal form A of compound 1 has good stability under conditions of high temperature, high humidity and strong light.

Test Example 1: In Vitro Assay

1. Experimental Objective:

The $IC_{50}$ values of the compounds in inhibiting uric acid reabsorption were determined using MDCK (canine kidney cell) cell line stably transfected with DRAT-1 (uric acid transporter) gene.

2. Background:

Gout is a progressive disease caused by abnormally elevated level of uric acid in blood. DRAT-1 gene encodes uric acid transporters existing in renal tubules. Small-molecule compounds can promote the excretion of uric acid by inhibiting the function of these transporters, thereby preventing the onset of gout.

3. Experimental Materials:

DRAT-1 (MDCK) cell line: MDCK cells stably transfected with URAT-1 gene.

Cell culture medium: MEM (minimum essential medium Eagle) medium supplemented with 10% FBS (fetal bovine serum), 1% sodium pyruvate and 250 μg/mL G418 (geneticin).

HBSS (Hank's balanced salt solution).

0.1 M NaOH solution.

$^{14}C$ labelled-uric acid solution.

$CO_2$ incubator.

Liquid scintillation counter Tri-Carb.

4. Experimental Procedure and Method:

4.1. Cell Inoculation:

1) The supernatant of the cell culture medium was removed by aspiration and the cells were rinsed with 10 mL PBS (phosphate buffered saline solution).

2) Preheated trypsin was added into the rinsed cell culture flask, and then the flask was rotated to make the trypsin evenly cover the bottom of the flask and the cells were digested at room temperature.

3) 10-15 mL of culture medium was used to suspend the cells in each T150 flask. 0.1 mL of the cells was sucked out and 2-fold diluted with trypan blue solution, and then the cells were counted.

4) The cells were diluted with culture medium to 2.5× $10^5$/mL, and the diluted cells were added into a 24-well plate (800 μL/well, 2×$10^5$ cells/well). The plate was placed in an incubator with 5% $CO_2$ at 37° C. overnight.

4.2 Cell Preparation:

1) After the cells were inoculated in the 24-well plate for 16-18 hours, the supernatant was discarded. HBSS buffer was added into each well to rinse the cells twice.

2) After aspirating the HBSS buffer, 180 μL of HBSS buffer was added into each well.

4.3 Preparation, Dilution and Addition of the Compound Solutions:

1) The compound powder was dissolved in 100% DMSO. The compound was 3-fold diluted to obtain six different concentrations, or 10-fold diluted to obtain two different concentrations, from a maximum initial concentration of 50 mM.

2) 5 μL of the DMSO solution obtained in step 1) was transferred into HBSS buffer to be 25-fold diluted.

3) 10 μL of the dilution obtained in step 2) was added into a 24-well cell plate, which was then placed in an incubator with 5% $CO_2$ at 37° C. for 15 minutes. The final concentration of DMSO was 0.2%. Cell control well: no compound added, only containing 0.2% DMSO.

4.4 Determination:

$^{14}C$ labelled-uric acid solution was diluted and added into the cell plate to obtain a final concentration of 50 μM. The cells were incubated in an incubator with 5% $CO_2$ at 37° C. for 10 minutes. After discarding the supernatant, the cells were rinsed twice with HBSS buffer. 0.1 M NaOH solution was added to lyse the cells. The cell lysates were collected and added into liquid scintillation vials. After adding the scintillation liquid, the signal was read in a liquid scintillation counter Tri-Carb.

4.5 Data Processing and Analysis:

According to the luminescent data, the inhibitory effect of the compounds on URAT-1 was analyzed, and the percent inhibition was calculated. $IC_{50}$ values were obtained using GraphPad Prism software to perform nonlinear fitting analysis on the percent inhibition (inh %). The experimental results are shown in the following Table 7.

TABLE 7

IC$_{50}$ results of the inhibitory effect of each embodiment on URAT-1

| No. | Compound | IC$_{50}$ |
|---|---|---|
| 1 | Amorphous form II of compound 1a | 8.0 μM |
| 2 | Amorphous form III of compound 1b | >20 μM |
| 3 | Amorphous form I of compound 1 | 10.36 μM |
| 4 | (±)-Lesinurad | 23.97 μM |

Conclusion: for the DRAT-1 (MDCK) cell line, compared with (±)-lesinurad, compound 1 and compound 1a show stronger inhibitory effect on the uric acid transport mediated by DRAT-1.

Test Example 2: In Vitro Assay

1. Experimental Objective:

The objective of this experiment is detect the metabolites of the compounds after incubation in human liver cells for 120 minutes using LC-UV-MS$^n$ (n=1-2). After data collection, MetaboLynx™ software was used to analyze MS and MS$^2$ data.

2. Experimental Method 2.1 Incubation System with Liver Cells

| | |
|---|---|
| Concentration of frozen liver cells | 1.0 × 10$^6$ cells/mL |
| Species | Human |
| Samples to be tested | (−)-WX001, (+)-WX002, (±)-lesinurad |
| Concentration of the samples to be tested | 10 μM |
| Incubation medium | William's E incubation medium |
| Incubation condition | 37° C., 5% CO$_2$/95% humidity |
| Incubation duration | 0, 120 min |
| Incubation volume | 200 μL |
| Positive control | 7-Ethoxycoumarin (7-EC, 30 μM) |

2.2 Sample Treatment and Analysis

After the cells were incubated with the samples for 2 hours, protein was precipitated using acetonitrile containing formic acid and then the mixture was centrifuged. The supernatant was taken out and blow-dried with nitrogen, and then redissolved and injected for analysis.

3. Experimental Result 3.1 The identification result of metabolites of compound 1a is shown in Table 8.

TABLE 8

| Metabolite | Retention time (min) | UV area percentage | Metabolic pathway |
|---|---|---|---|
| Compound 1a | 9.71 | 100% | NA |

3.2 The identification result of metabolites of compound 1b is shown in Table 9

TABLE 9

| Metabolite | Retention time (min) | UV area percentage | Metabolic pathway |
|---|---|---|---|
| Compound 1b | 9.71 | 100% | NA |

3.3 The identification result of metabolites of (±)-lesinurad is shown in Table 10.

TABLE 10

| Metabolite | Retention time (min) | UV area percentage | Metabolic pathway |
|---|---|---|---|
| (±)-Lesinurad-M1 | 6.26 | 4.40% | oxidation |
| (±)-Lesinurad | 9.02 | 95.60% | NA |

4. Experimental Conclusion:

Experimental results showed that, under the same metabolic condition in human liver cells, compound (±)-lesinurad produced 4.40% of the metabolite Ml, while no metabolite was detected in the study of the amorphous form II of compound 1a and the amorphous form III of compound 1b. Compared with (±)-lesinurad, compound 1a and compound 1b exhibit improved in vitro stability in liver cells.

Test Example 3: In Vivo Assay

1. Experimental Objective

The pharmacokinetic behavior and characteristics of the compounds of the present disclosure in cynomolgus monkeys was studied, using cynomolgus monkeys as experimental animals and determining the concentrations of compound 1a, compound 1b, compound 1 and (±)-lesinurad in plasma at different time points by LC/MS/MS method after administering compound 1a (crystal form B), compound 1b (crystal form C), compound 1 (crystal form A) and (±)-lesinurad through IV (intravenous injection) and PO (nasal feeding) to cynomolgus monkeys.

2. Experimental Method 2.1 Experimental Compounds

Compound 1a (crystal form B), compound 1b (crystal form C), compound 1 (crystal form A) and (±)-lesinurad 2.2 Experimental Animals 24 healthy adult male cynomolgus monkeys were divided into 8 groups (there were IV and PO groups for each compound) with 3 animals per group.

2.3 Drug Preparation

An appropriate amount of the samples was weighted and dissolved in a certain amount of DMSO by ultrasound, followed by addition of PEG400 solution to obtain clear solutions (DMSO/PEG400/H$_2$O (5/40/55)) of the compounds to be tested with a concentration of 2 mg/mL for IV administration.

An appropriate amount of the samples was weighted and dissolved in a certain amount of DMSO by ultrasound, followed by addition of 0.5% MC solution to obtain suspensions (DMSO/0.5% MC (5/95)) of the compounds to be tested with a concentration of 2 mg/mL for PO administration.

2.4 Administration 24 male cynomolgus monkeys were divided into 8 groups with 3 animals per group, and the drugs were administered through IV and PO after the animals had been fasting overnight. The dose for IV administration was 2 mg/kg and the dosing volume was 1 mL/kg; the dose for PO administration was 10 mg/kg and the dosing volume was 5 mL/kg.

3. Experimental Operation

In the IV administration groups, approximately 200 μL of blood was collected 0.083, 0.25, 0.5, 1, 2, 4, 6, 8, and 24 hours after administration; the collected blood samples were added into anticoagulation tubes containing K2-EDTA and centrifuged at 3000 rpm for 15 minutes; the plasma was isolated and stored at −80° C. In the PO administration groups, the blood was collected 0.25, 0.5, 1, 2, 4, 6, 8, and 24 hours after administration, and other operations were the same as in the IV administration group. After the plasma samples were pre-treated to precipitate the protein, the drug concentration in the plasma was determined by LC/MS/MS method. The linear range of the analysis method was 20.00-6000 nM. In PO administration group, urine was collected 0-24 hours after administration, and the drug concentration in the urine was determined by LC/MS/MS method. The linear range of the analysis method was 20.00-6000 nM.

4. Pharmacokinetic Parameters

The experimental results show that compound 1a (crystal form B), compound 1b (crystal form C), compound 1 (crystal form A) and (±)-lesinurad exhibit different pharmacokinetic behaviors in cynomolgus monkeys. When administered at a same dose through PO, compared with (±)-lesinurad, compound 1a (crystal form B), compound 1b (crystal form C), and compound 1 (crystal form A) exhibit higher plasma exposure and better overall pharmacokinetic behavior. Compared with (±)-lesinurad, compound 1a (crystal form B) and compound 1 (crystal form A) also exhibit higher effective coverage rates (0-24 h) of the target by the concentration of the compounds in urine. Note: the effective coverage rate of the target by the concentration of the compound in urine= mean drug concentration in urine (0-24 h)/IC$_{50}$ of the drug on the URAT1 target. Moreover, no mutual transformation between the two axially chiral isomers 1a and 1b was observed in vivo, and they were retained as stable single axially chiral isomer in circulation system. In addition, the experimental results are shown in the following Table 11.

2. Experimental Procedure and Method:

The cell culture medium used in the intake inhibition experiment was DMEM (cell essential medium culture medium) supplemented with 10% FBS (containing penicillin and streptomycin). The cell line overexpressing human drug transporter (MDCK-OAT4) and cells with empty vector (MDCK-pcDNA3.1) were recovered and subcultured, and then adherent cells in good growth state were selected and digested with trypsin to disperse into single cell suspensions. The cell suspensions were adjusted to obtain a density of 2.0-3.0×10$^5$ cells/mL with medium, and then inoculated into 24-well cell culture plates in an amount of 1 mL/well. The cells were cultured in an incubator with 5% CO$_2$ and saturated air humidity at 37° C. for 2-3 days, after which the cells grew over the wells. The culture medium was removed from the culture plates and the cells were washed once with Hanks buffered saline solution (without Cl$^-$) or PBS. Subsequently, 37° C. Hanks buffered saline solution (without Cl$^-$) or PBS buffered saline solution was added into each well and the cells were incubated for 10 minutes. Then the Hanks buffered saline solution (without Cl$^-$) or PBS buffered saline solution in the 24-well plates was replaced with 500 μL of radiolabeled probe substrate solution and the administration was started. After completion of the administration (2 min), the reaction was terminated with respective pre-cooled buffer saline solution, and the cells were rinsed for 3 times. 400 μL of 0.1 mmol/L NaOH was added to each well to lyse the cells. The cell lysates were added into scintillation vials, followed by addition of 3 mL of Aquasol-2 scintillation solution. The intensity of radioactivity in the samples was measured by a Tri-Carb 2910TR liquid scintillator. Three wells (n=3) were set for each drug concentration, positive control and blank control (mock) in the cell transport assay.

3. Data Processing:

The uptake value of the transporter cells in the group containing only the radiolabeled substrate (deducting the uptake value U$_0$ cells with empty vector in the background

TABLE 11

Pharmacokinetic parameters of each embodiment in cynomolgus monkeys

| | Test example | | Compound 1 (crystal form A) | Compound 1a (crystal form B) | Compound 1b (crystal form C) | (±)-Lesinurad |
|---|---|---|---|---|---|---|
| IV | Actual dose | Mg/kg | 2.00 | 1.77 | 2.10 | |
| | Initial concentration | C$_0$ (nM) | 42185 | 32033 | 42077 | |
| | Half-life | T$_{1/2}$ (h) | 3.61 | 3.39 | 4.28 | |
| | Apparent volume of distribution | Vd$_{ss}$ (L/Kg) | 1.09 | 0.533 | 0.661 | |
| | Clearance rate | Cl (mL/min/Kg) | 4.20 | 4.88 | 4.78 | |
| | Area under the curve | AUG$_{0-inf}$ (nM · h) | 18389 | 15709 | 16092 | |
| | Residence time | MRT$_{0-inf}$ (h) | 4.01 | 1.83 | 2.34 | |
| PO | Actual dose | Mg/kg | 10.2 | 7.63 | 10.6 | 9.91 |
| | Peak concentration | C$_{max}$ (nM) | 46100 | 22600 | 13173 | 37233 |
| | Time to peak | T$_{max}$ (h) | 0.83 | 1.33 | 2.33 | 0.58 |
| | Half-life | T$_{1/2}$ (h) | 3.34 | 4.10 | 4.46 | 3.78 |
| | Area under the curve | AUG$_{0-inf}$ (nM · h) | 120062 | 89770 | 62456 | 69300 |
| | Residence time | MRT$_{0-inf}$ (h) | 3.76 | 4.65 | 5.74 | 3.44 |
| | Bioavailability | F (%) | 131% | 132 | 77.6 | |
| | Mean drug concentration in urine (0-24 h) | C$_{urine, 0-24 h}$ (nM) | 38915 | 54403 | 7976 | 71622 |
| | Coverage of the target by mean drug concentration in urine (0-24 h)/IC$_{50}$ | Fold | 3.8 | 6.8 | 0.4 | 3.0 |

Test Example 4: In Vitro Assay

1. Experimental Objective:

The IC$_{50}$ values of the compounds in inhibiting reabsorption of specific substrates were determined using MDCK (canine kidney cell) cell line stably transfected with OAT-4 (organic anion transporter-4) gene.

group) was defined as 100% (control, Uc), which was counted as a standard for the calculation of the percentage (%) of the intake value U (after deducting the background) in each administration group after adding the tested compounds against the intake value Uc in the control group, and the inhibitory rate (IR) of each concentration on the activity of the transporter was calculated to express the extent of the inhibitory effect of the compounds on the transporters. The calculation formula is as follows:

$IR=1-[100\times(U-U0)/(Uc-U0)]\%$

Three repetitions were set for each drug concentration (i.e., n=3). Mean±standard error (SD) was calculated using the statistical formula in Microsoft® Excel 2010 software. According to the inhibitory rate (IR) of each concentration on each transporter, the $IC_{50}$ of each compound on the transport activity of the drug transporter was calculated by Prism5.0 and the Forecast function in Microsoft® Excel 2010 software.

The experimental results are shown in Table 12:

TABLE 12

$IC_{50}$ results of the inhibitory effect of each embodiment on OAT-4

| No. | Compound | $IC_{50}$ of the inhibition on URAT-1 transporting substrate $^{14}C$-UA ($^{14}C$-uric acid) data see table 7 | $IC_{50}$ of the inhibition on OAT-4 transporting different substrates | |
|---|---|---|---|---|
| | | | $^{14}C$-UA ($^{14}C$-uric acid) | $^{3}H$-ES ($^{3}H$-estrone ammonium sulfate) |
| 1 | Amorphous form I of compound 1 | 10.36 µM | 7.92 µM | 17.09 µM |
| 2 | (±)-Lesinurad | 23.97 µM | 2.17 µM | 12.74 µM |

Conclusion: on the OAT4-4 (MDCK) cell line, compound 1 exhibits a weaker inhibitory effect than (±)-lesinurad on the transport of the two different substrates (uric acid and estrone sulfate ammonium salt) mediated by OAT-4.

Since both OAT-4 and DRAT-1 are located in the brush border membrane of epithelial cells of renal tubules, the compounds are capable of simultaneously inhibiting these two transporters. Therefore, by comparing the $IC_{50}$ of the compounds in inhibiting $^{14}C$-uric acid transport mediated by URAT-1 and the $IC_{50}$ of the compounds in inhibiting $^{14}C$-uric acid and $^{3}H$-estrone sulfate ammonium salt transport mediated by OAT-4, it is found that: while (±)-lesinurad produces effective inhibition of URAT-1 mediated uric acid transport, it produces stronger inhibition on OAT-4 mediated uric acid transport (11 times) and on OAT-4 mediated estrone sulfate ammonium salt transport (2 times); on the contrary, while compound 1 produces effective inhibition of DRAT-1 mediated uric acid transport, it only produces comparable inhibition (1 time) on OAT-4 mediated uric acid transport and weaker inhibition of OAT-4 mediated estrone sulfate ammonium salt transport (0.6 time). As the OAT-4 transporter plays an important role in maintaining normal function of human bodies, (±)-lesinurad has a certain degree of safety risk for its strong preferential inhibition of the OAT-4 transporter, while compound 1 shows higher safety for its relatively weak inhibition of the OAT-4 transporter.

What is claimed is:

1. A crystal form A of compound 1, wherein the crystal form A of compound 1 has an X-ray powder diffraction pattern comprising characteristic diffraction peaks at angle 2θ of 7.16±0.2°, 17.98±0.2°, and 22.30±0.2°;

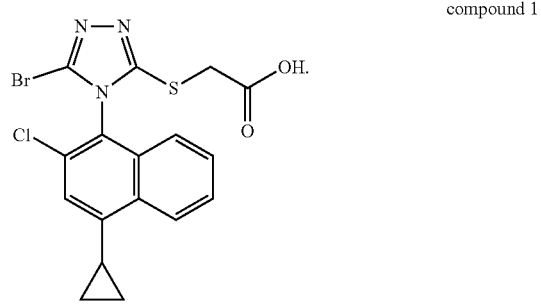 [SMILES: O=C(O)CSc1nnc(Br)n1-c1c(Cl)cc(C2CC2)c2ccccc12]

compound 1

2. The crystal form A of compound 1 as defined in claim 1, wherein the crystal form A of compound 1 has an X-ray powder diffraction pattern comprising characteristic diffraction peaks at angle 2θ of 7.16±0.2°, 12.50±0.2°, 14.61±0.2°, 17.98±0.2°, 19.62±0.2°, 22.30±0.2°, 24.63±0.2°, and 26.37±0.2°.

3. The crystal form A of compound 1 as defined in claim 2, wherein the crystal form A of compound 1 has an X-ray powder diffraction pattern comprising characteristic diffraction peaks at angle 2θ of 7.16±0.2°, 9.56±0.2°, 11.30±0.2°, 12.50±0.2°, 14.61±0.2°, 17.98±0.2°, 18.72±0.2°, 19.62±0.2°, 22.30±0.2°, 24.63±0.2°, and 26.37±0.2°.

4. The crystal form A of compound 1 as defined in claim 3, wherein the crystal form A of compound 1 has an X-ray powder diffraction pattern as shown in FIG. 1.

5. The crystal form A of compound 1 as defined in claim 1, wherein the crystal form A of compound 1 has a differential scanning calorimetry curve comprising an endothermic peak with an onset at 167.42° C.±2° C.;

or, the crystal form A of compound 1 has a thermogravimetric analysis curve showing a weight loss of 0.3708% occurred at 143.64° C.±3° C.

Figure 2:
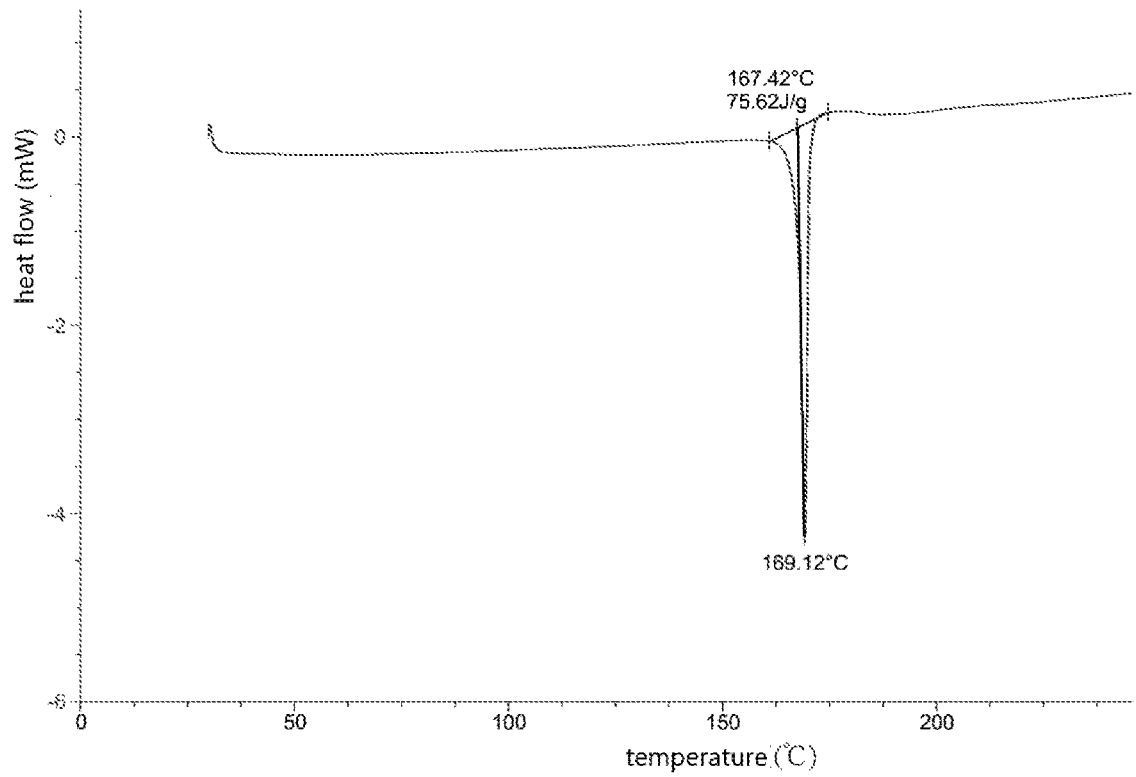
FIG. 2 is the DSC pattern of the crystal form A of compound 1.
Figure 3:
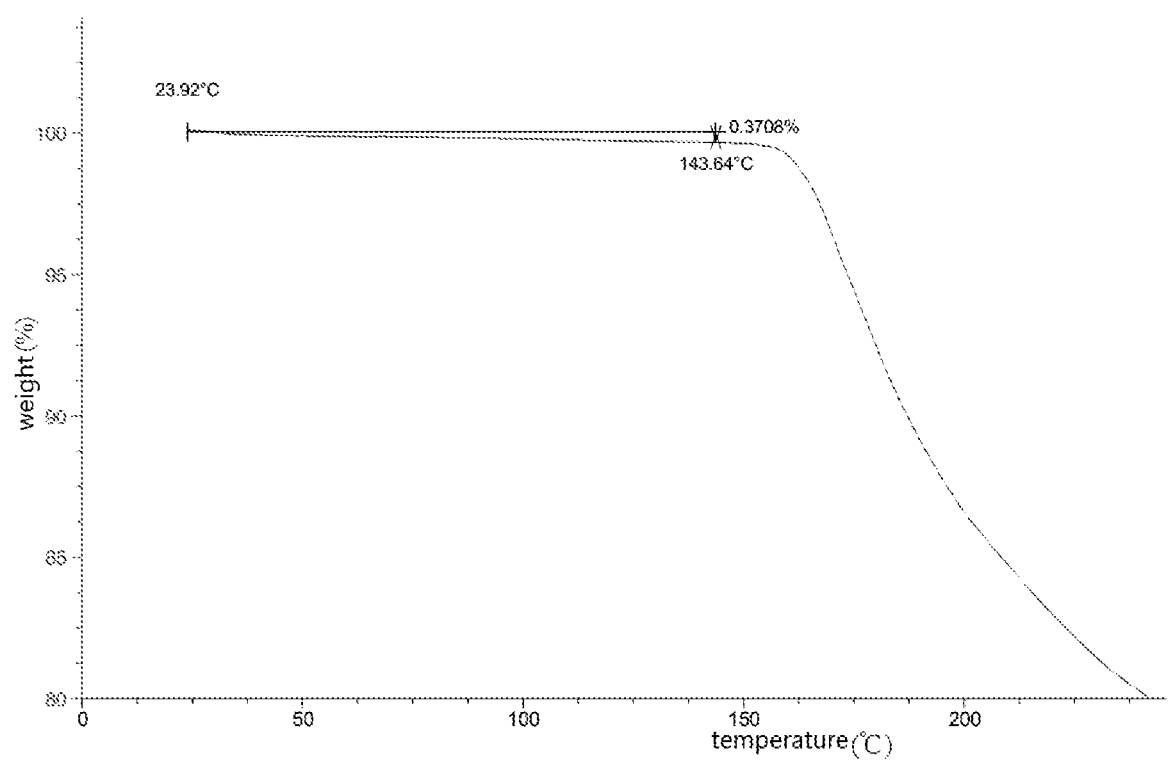
FIG. 3 is the TGA pattern of the crystal form A of compound 1.
Figure 4:
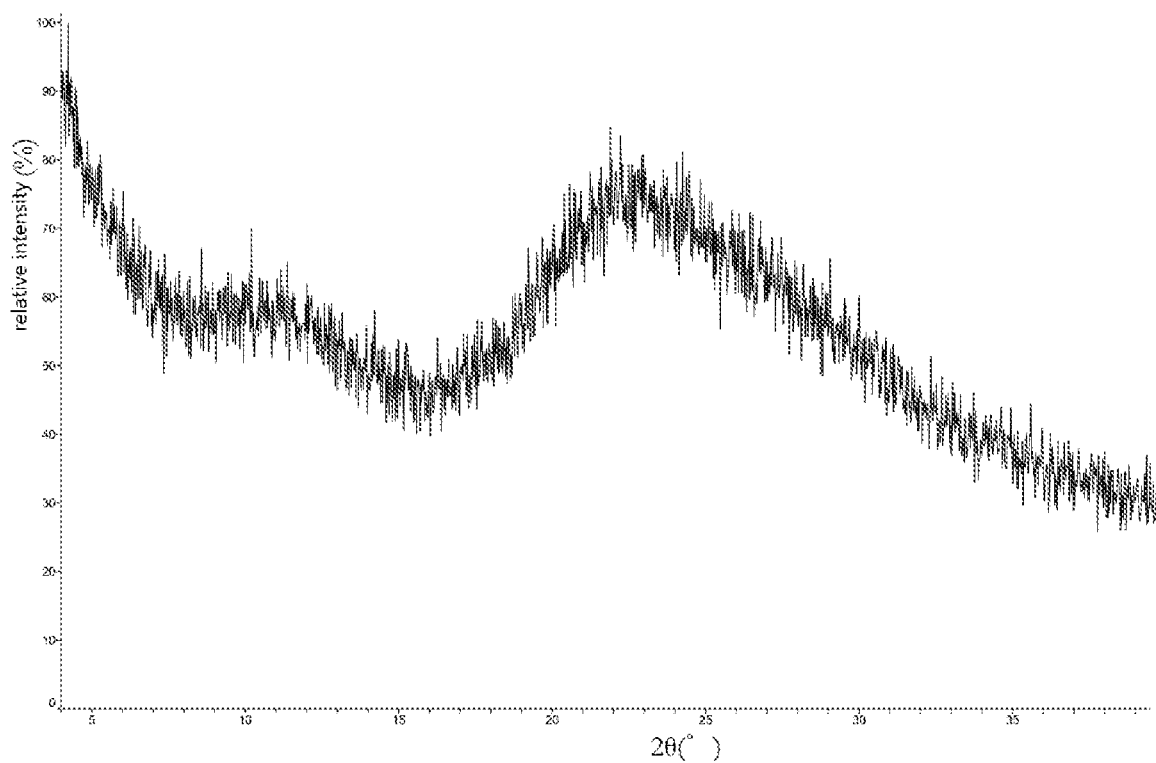
FIG. 4 is the XRPD pattern of the amorphous form I of compound 1 measured by Cu-Kα radiation.
Figure 5:
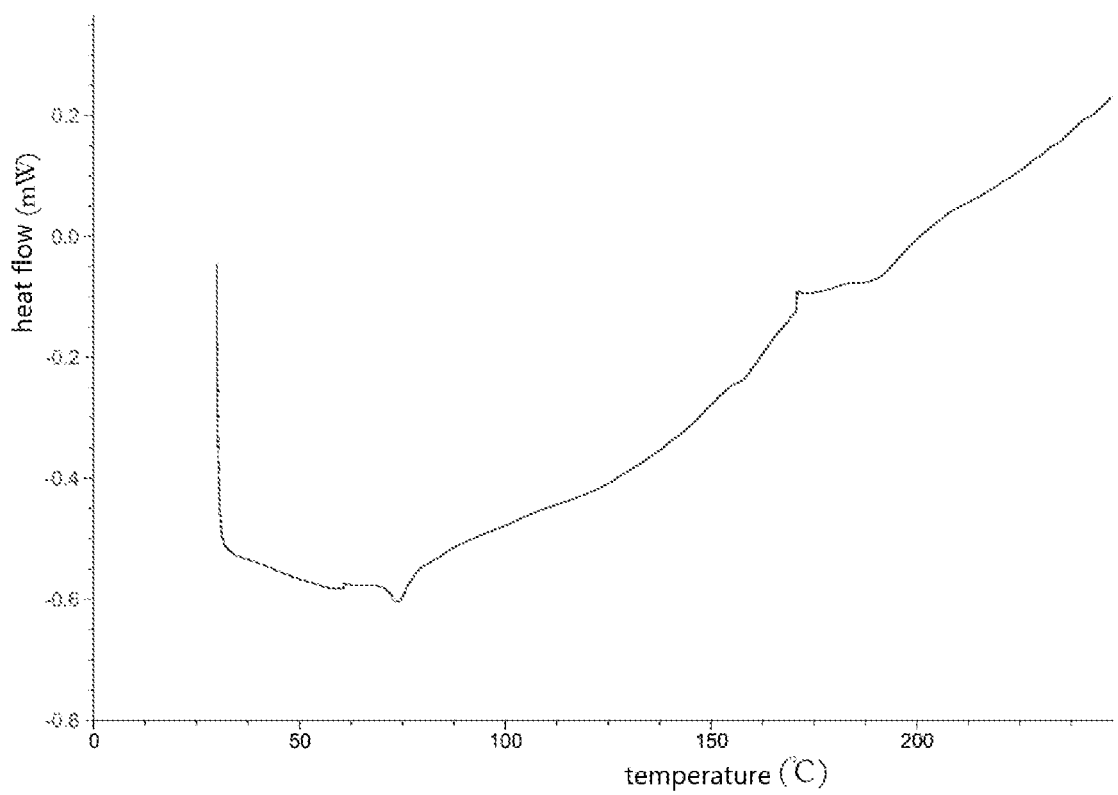
FIG. 5 is the DSC pattern of the amorphous form I of compound 1.
Figure 6:
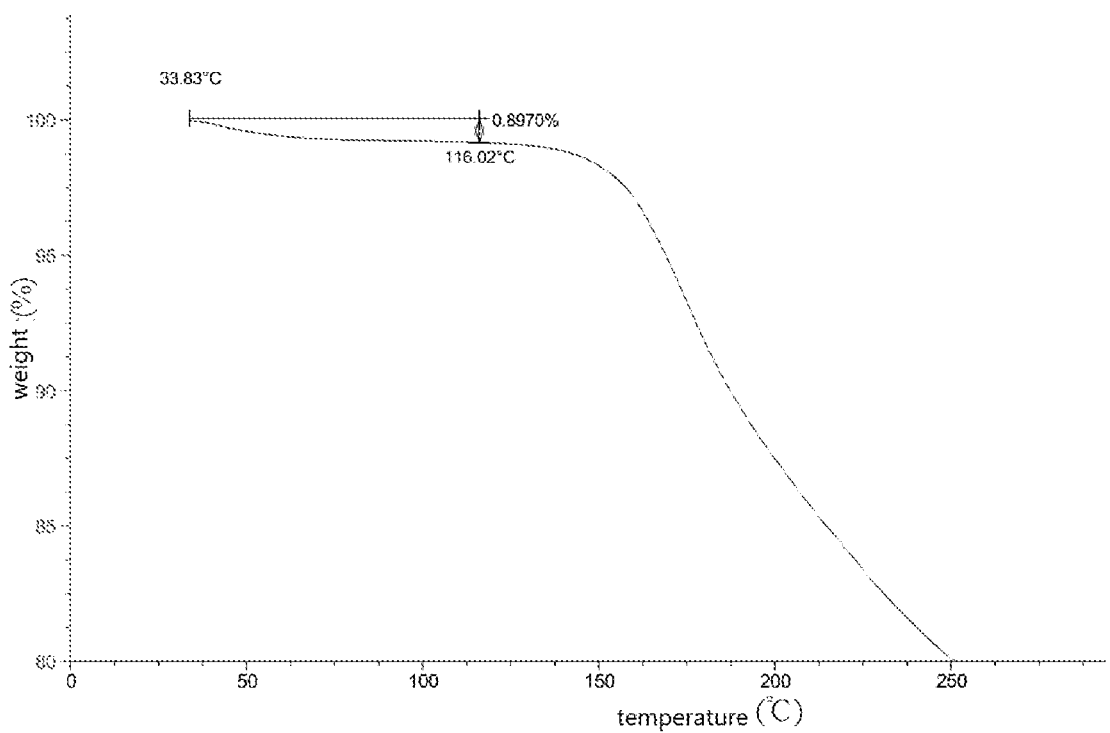
FIG. 6 is the TGA pattern of the amorphous form I of compound 1.
Figure 7:
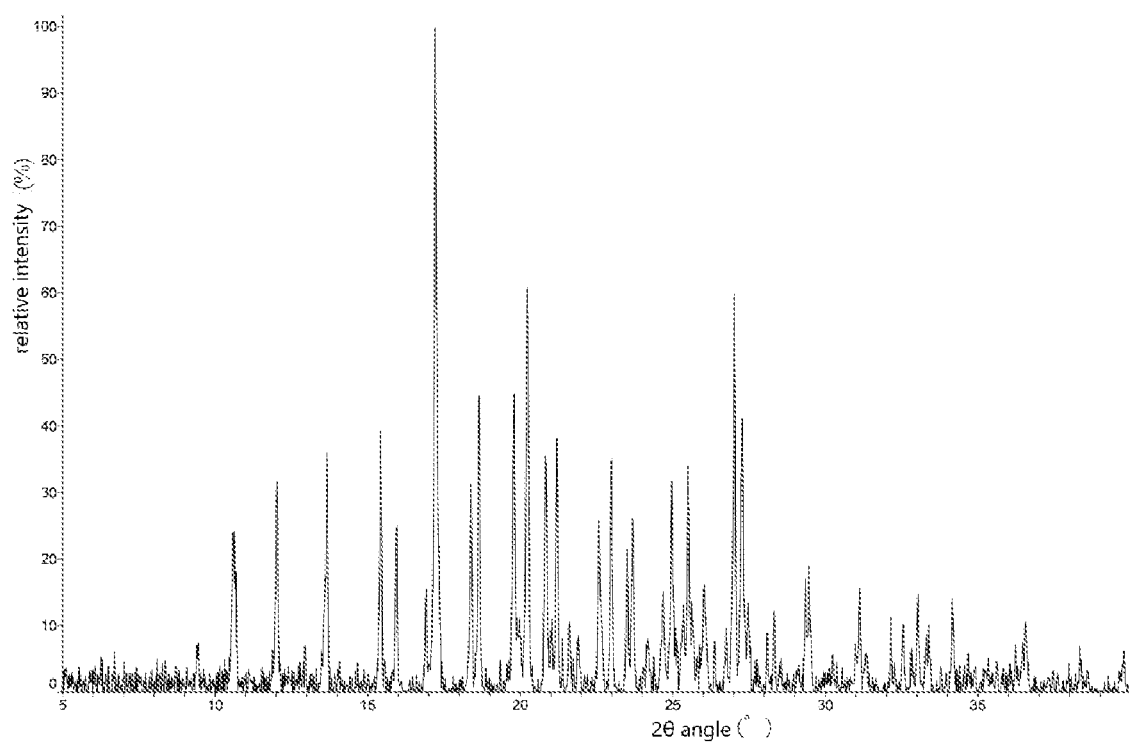
FIG. 7 is the XRPD pattern of the crystal form B of compound 1a measured by Cu-Kα radiation.
Figure 8:
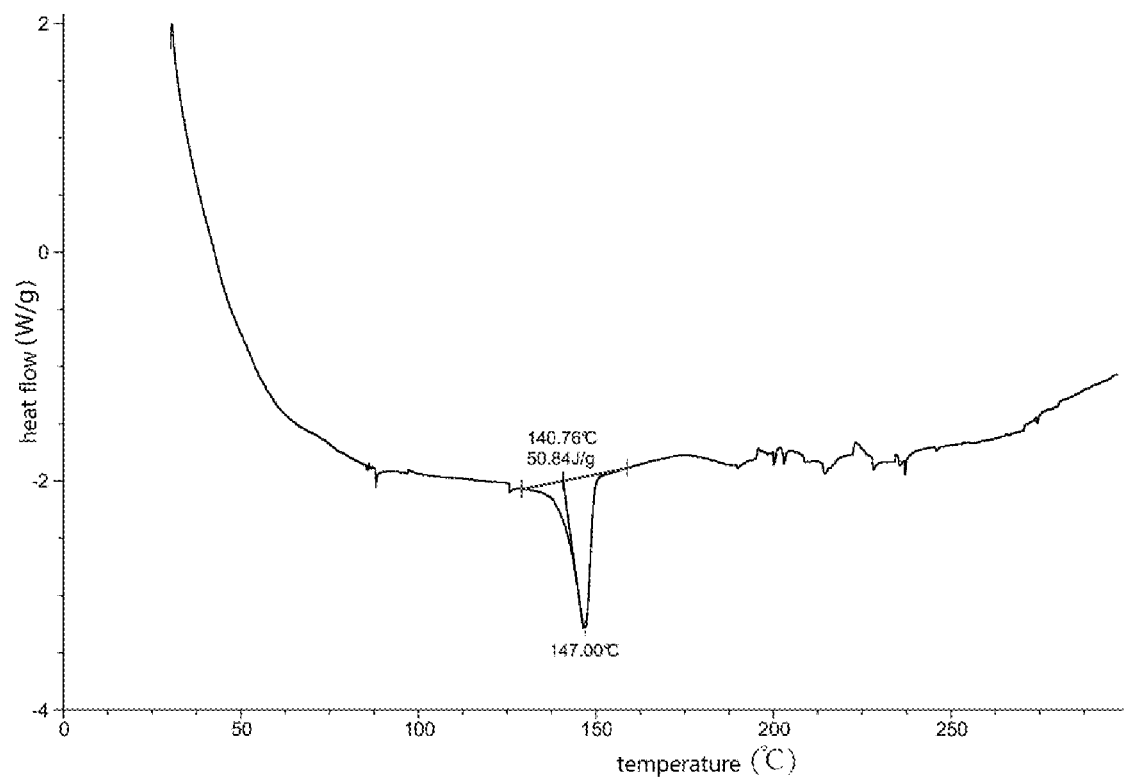
Figure 9:
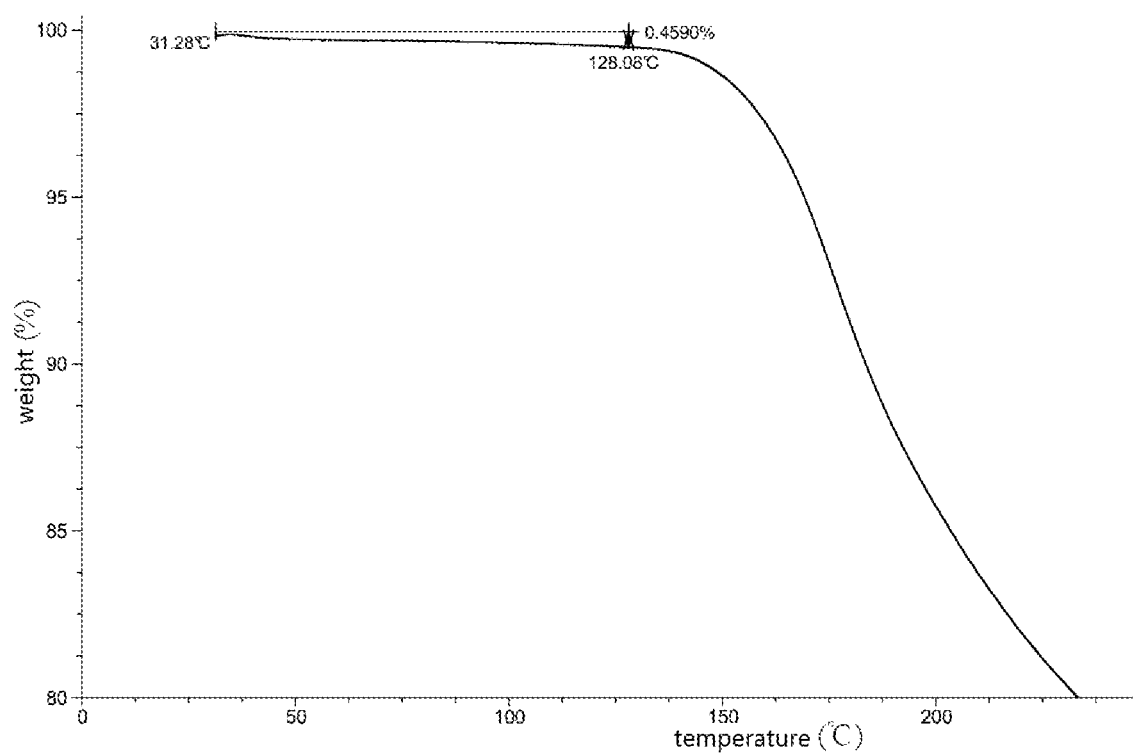
Figure 10:
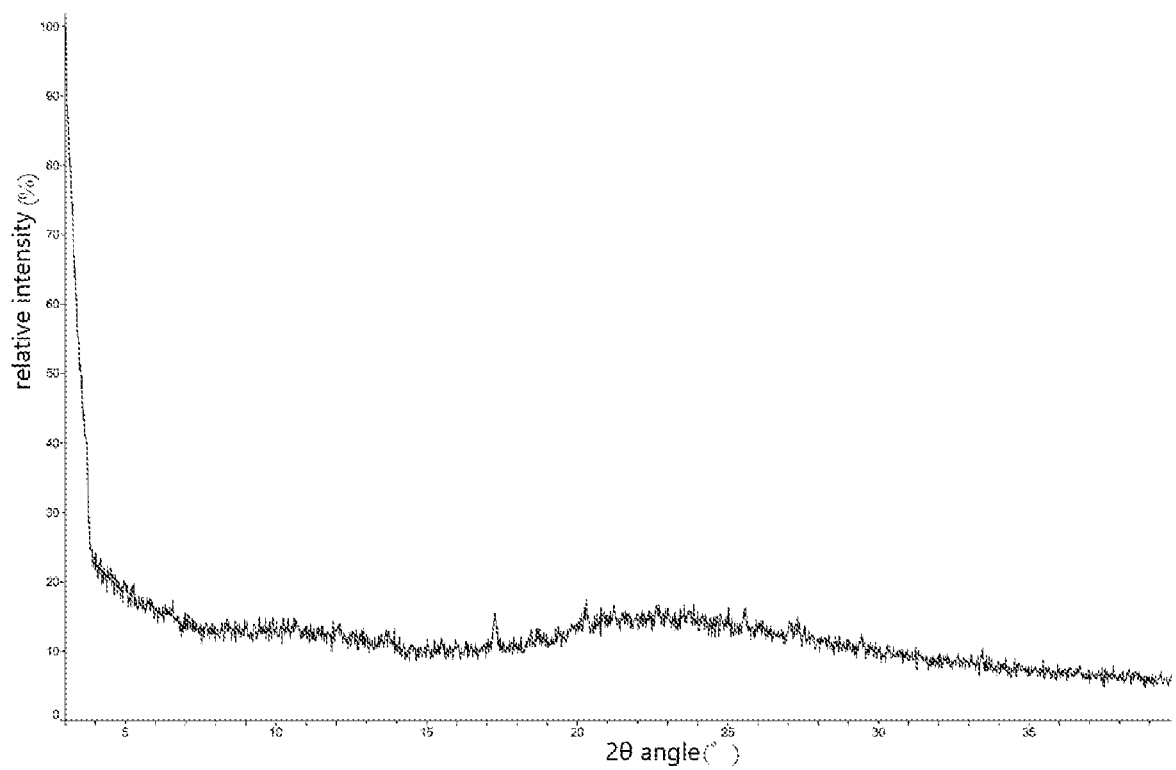
FIG. 10 is the XRPD pattern of the amorphous form II of compound 1a measured by Cu-Kα radiation.
Figure 11:
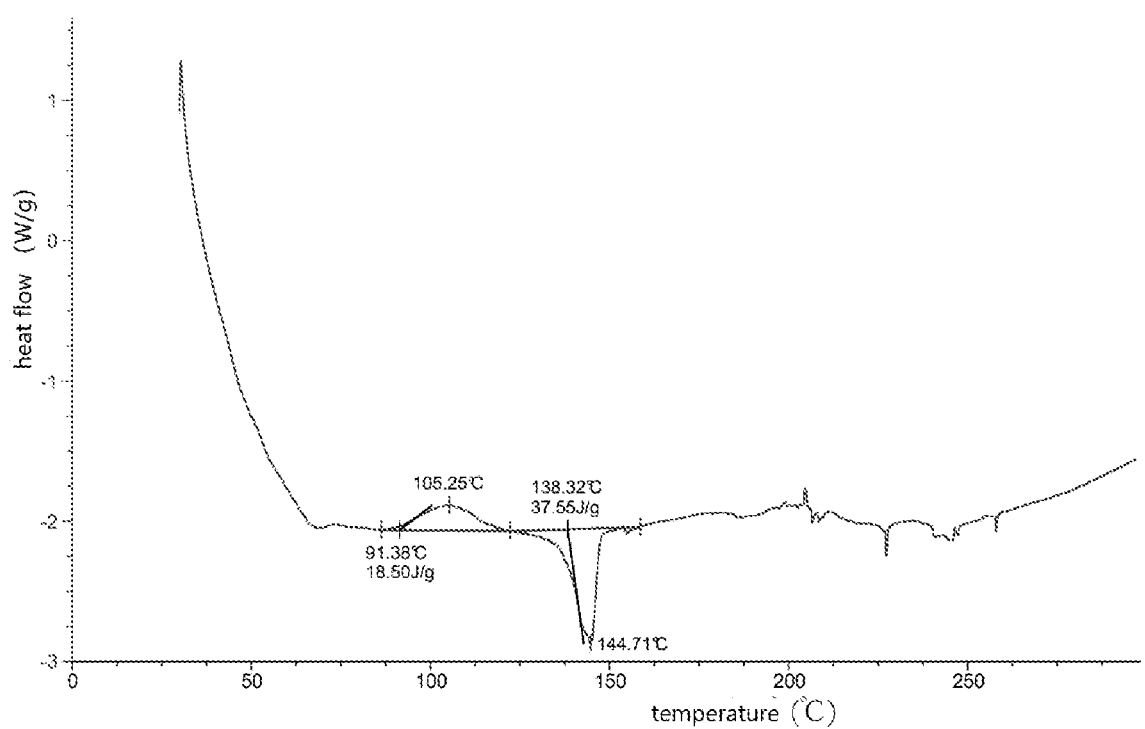
Figure 12:
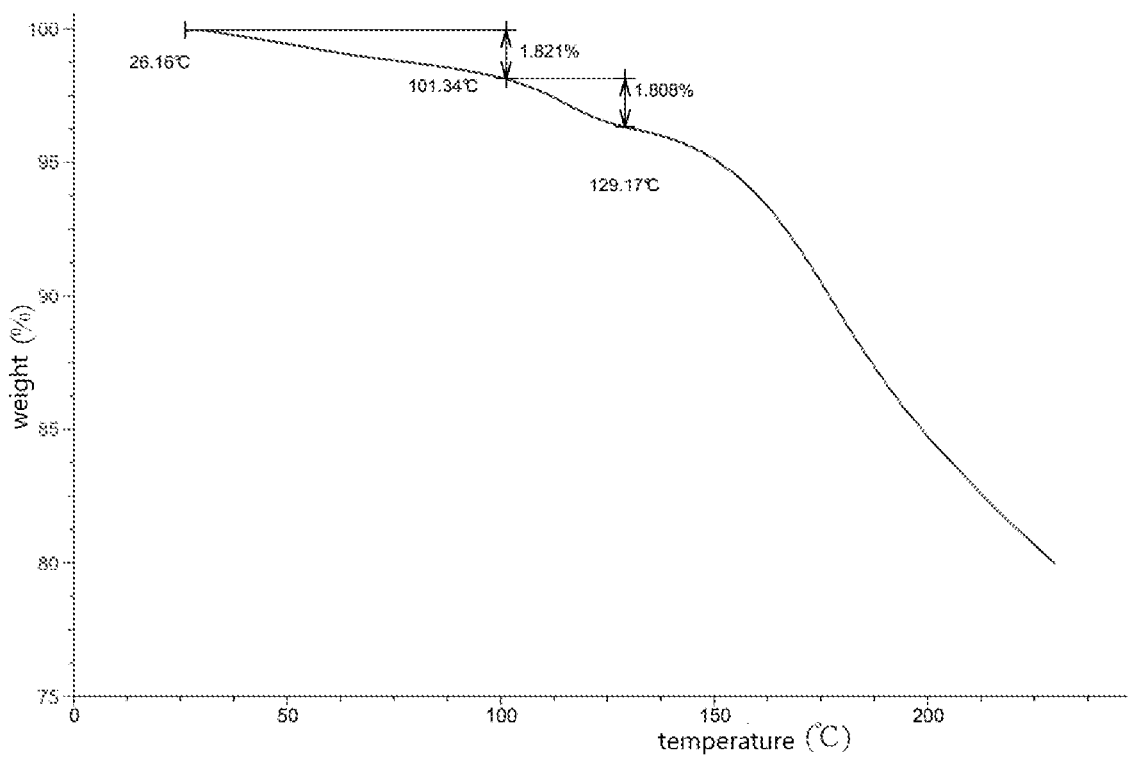
Figure 13:
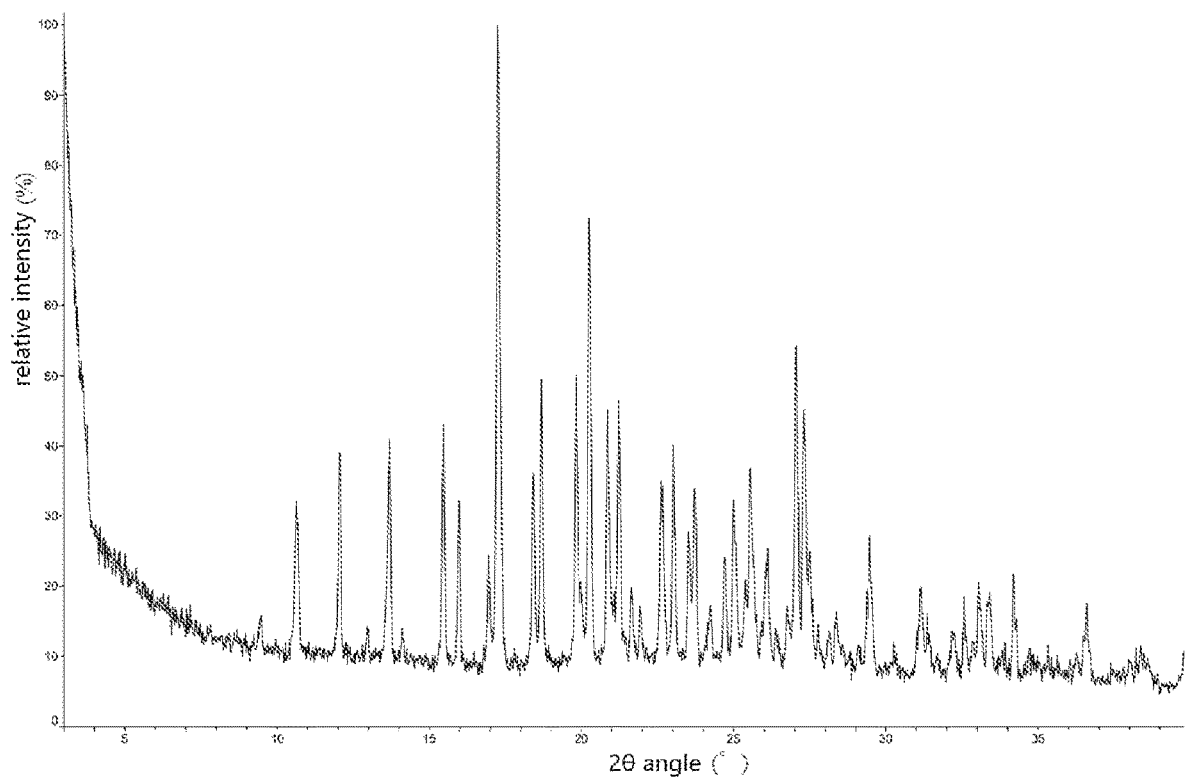
FIG. 13 is the XRPD pattern of the crystal form C of compound 1b measured by Cu-Kα radiation.
Figure 14:
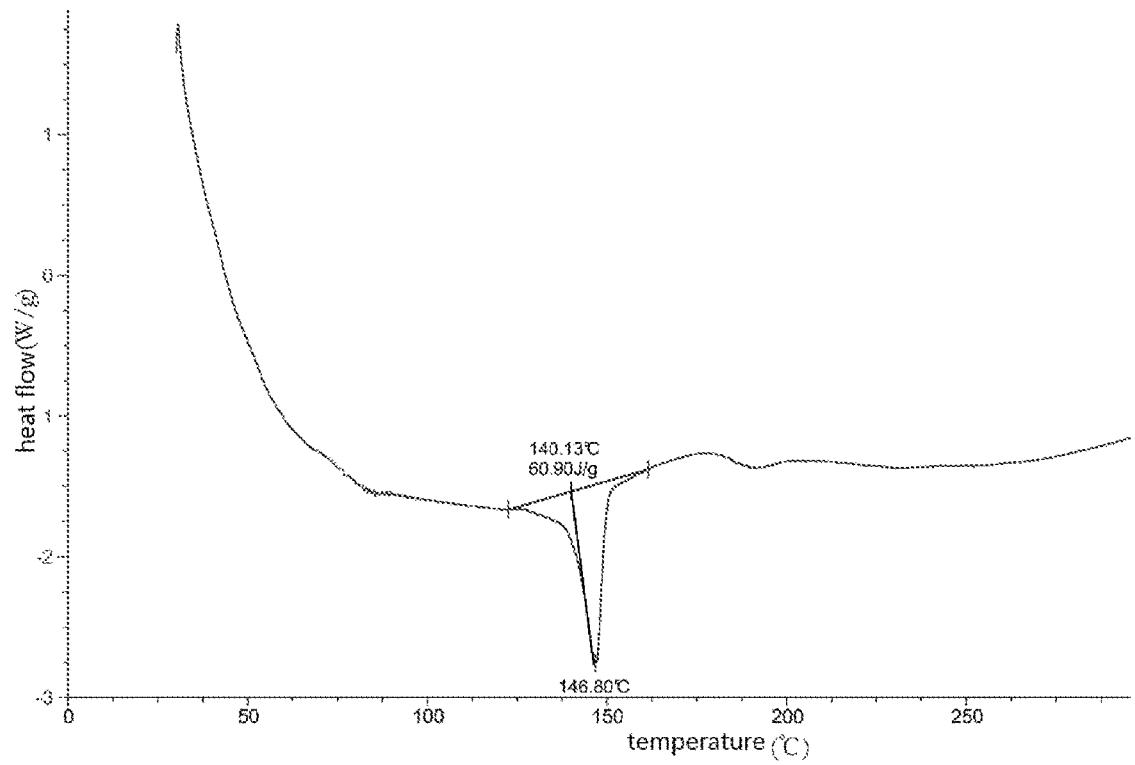
FIG. 14 is the DSC pattern of the crystal form C of compound 1b.
Figure 15:
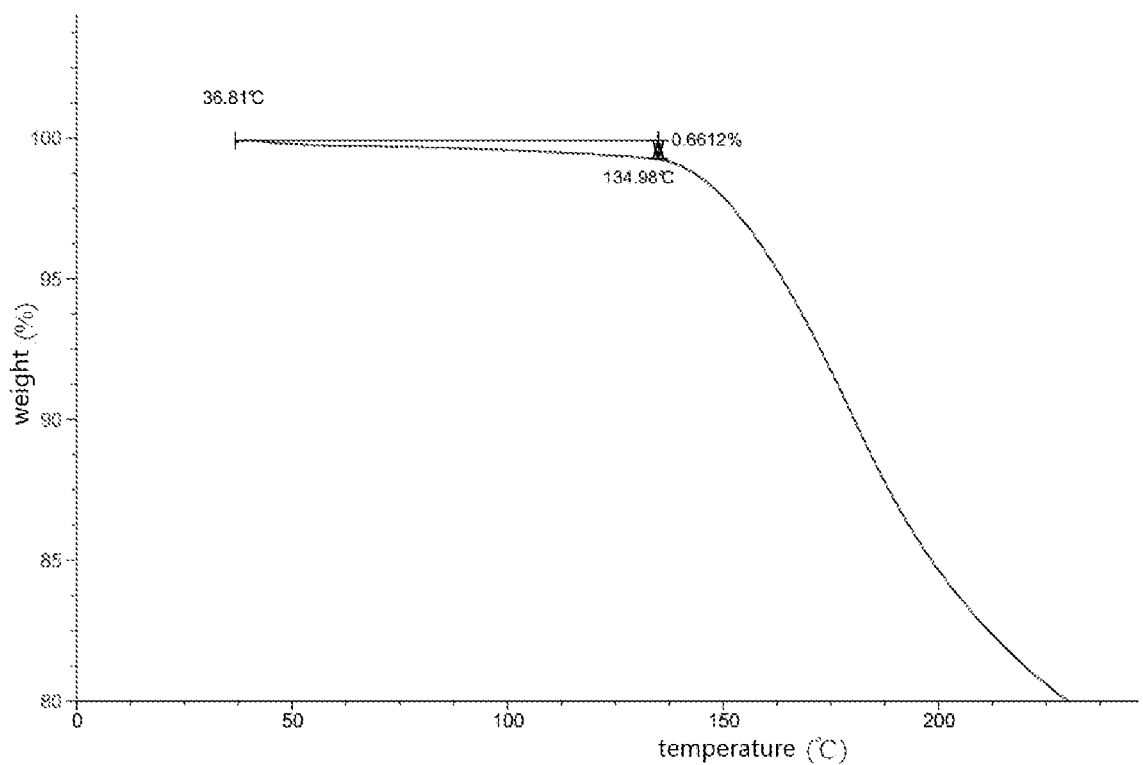
FIG. 15 is the TGA pattern of the crystal form C of compound 1b.
Figure 16:
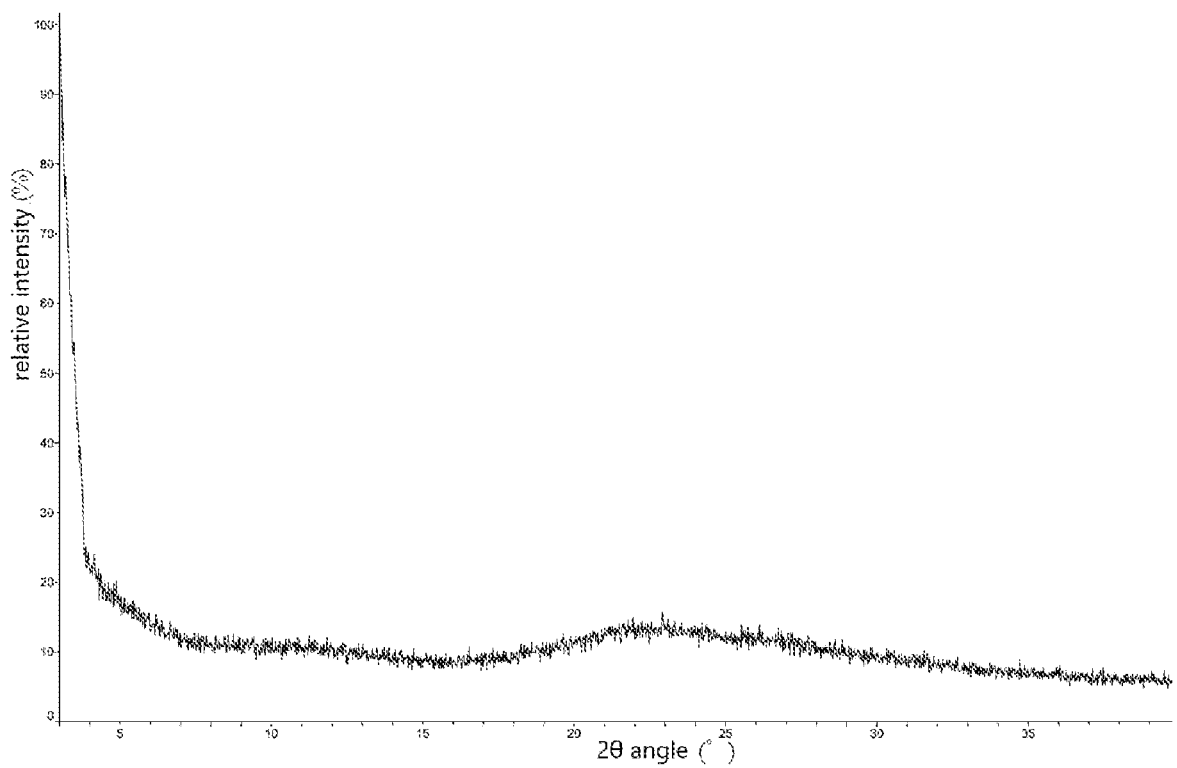
FIG. 16 is the XRPD pattern of the amorphous form III of compound 1b measured by Cu-Kα radiation.
Figure 17:
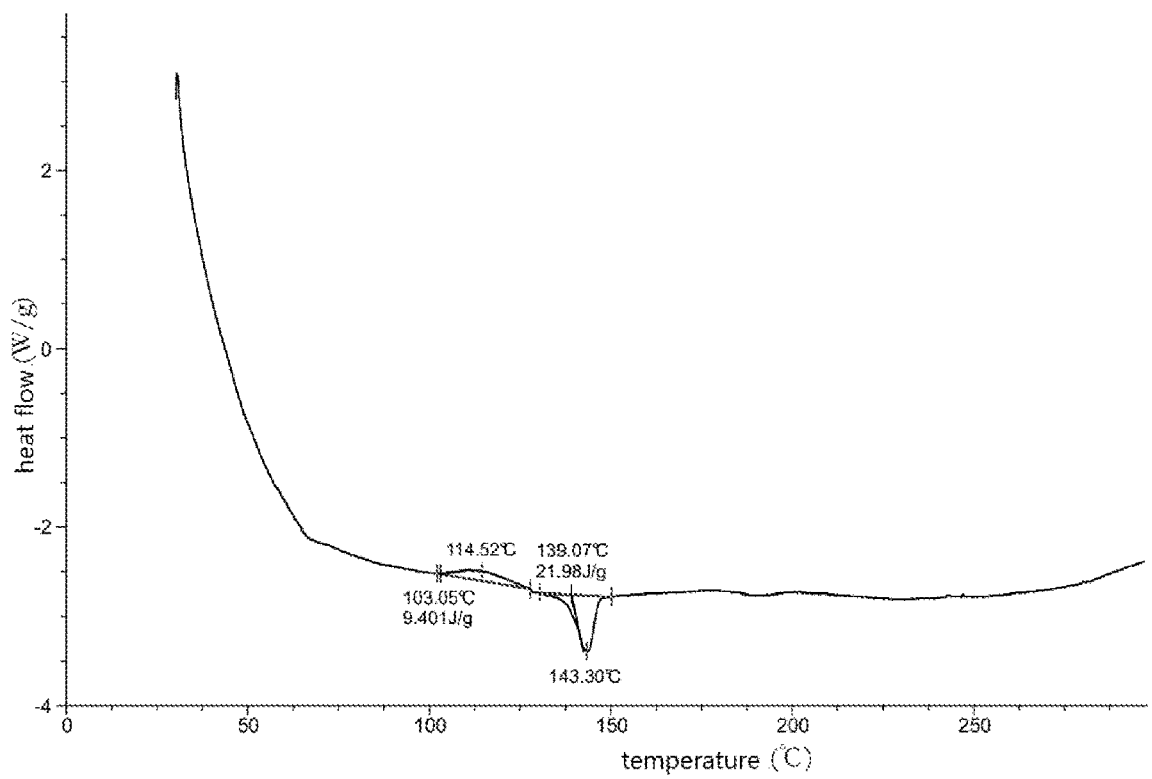
FIG. 17 is the DSC pattern of the amorphous form III of compound 1b.
Figure 18:
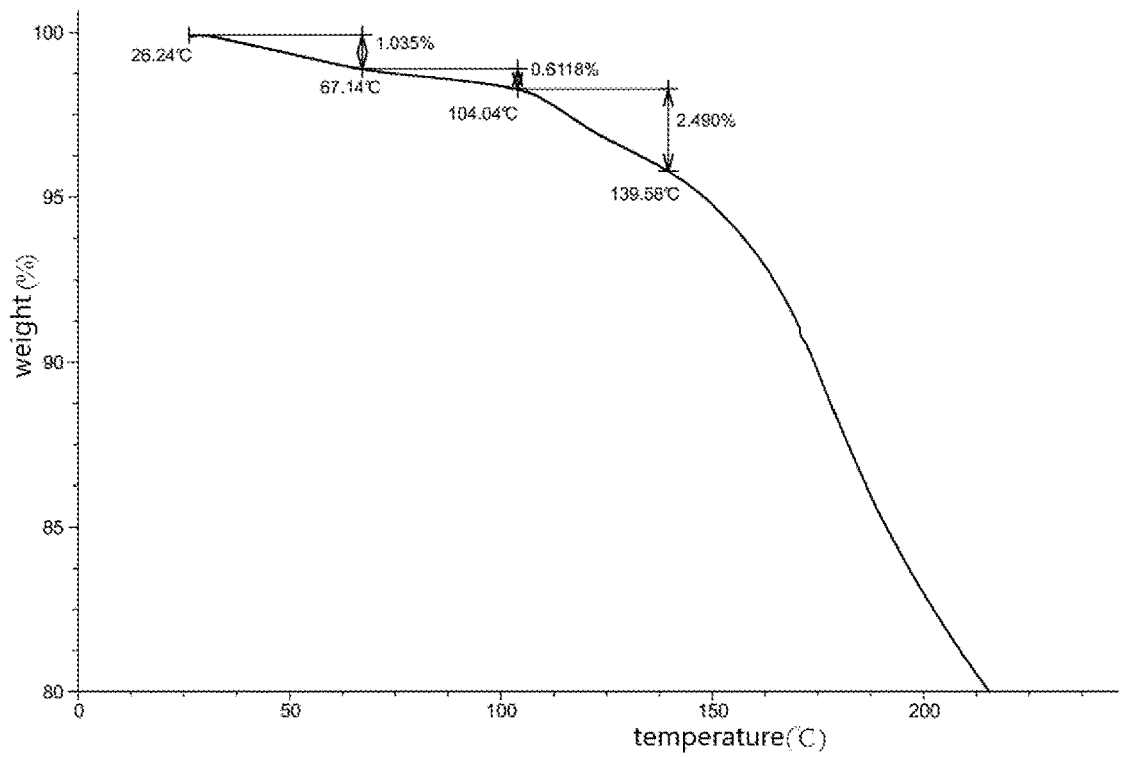
FIG. 18 is the TGA pattern of the amorphous form III of compound 1b.
Figure 19:
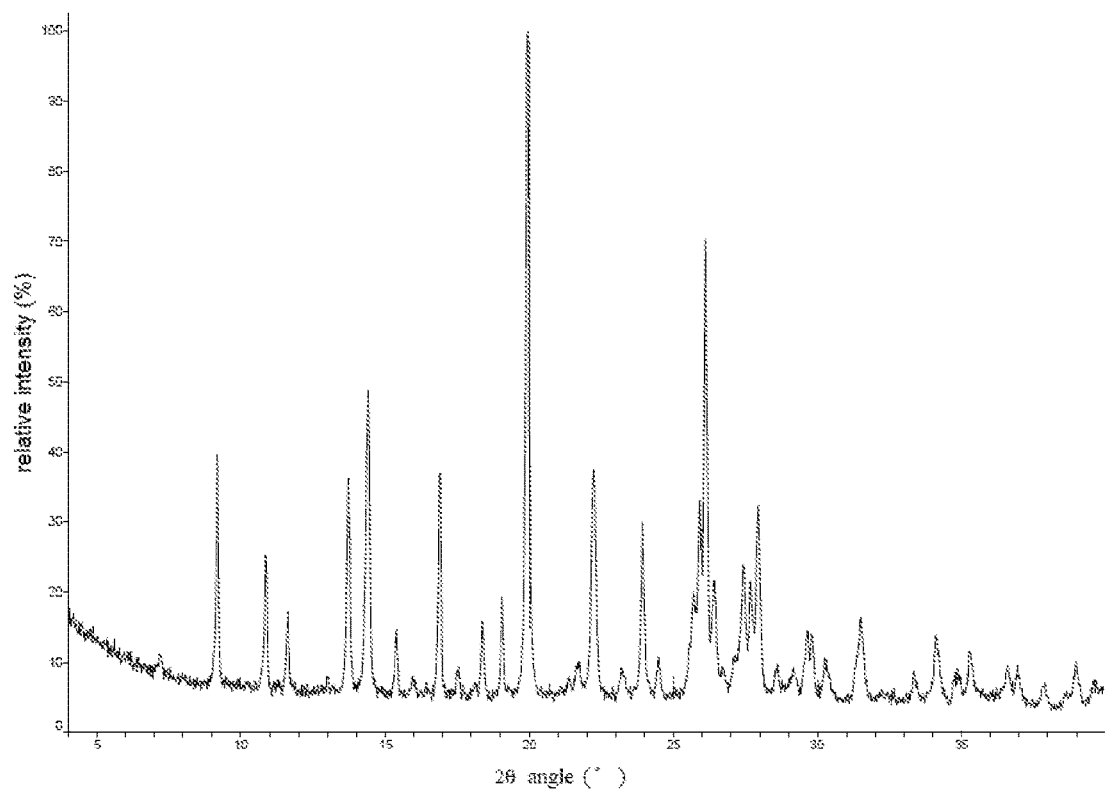
FIG. 19 is the XRPD pattern of the crystal form D of compound 1 measured by Cu-Kα radiation.
Figure 20:
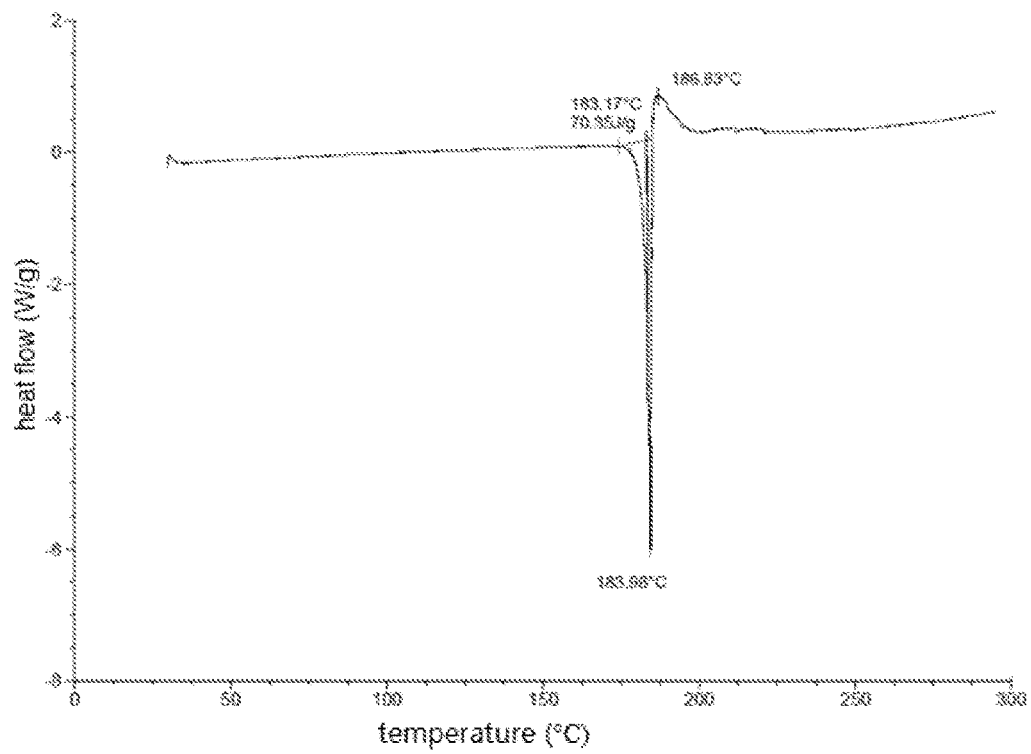
FIG. 20 is the DSC pattern of the crystal form D of compound 1.
Figure 21:
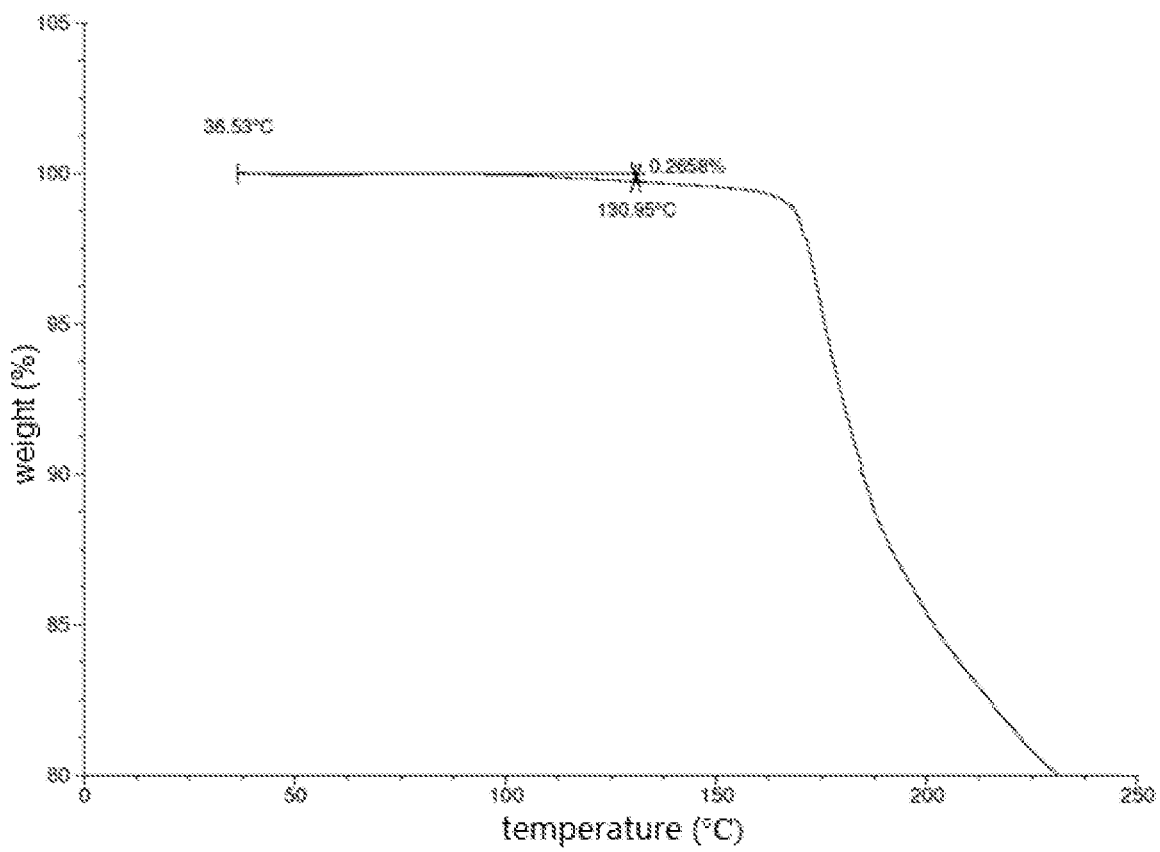
FIG. 21 is the TGA pattern of the crystal form D of compound 1.

6. The crystal form A Of compound 1 as defined in claim 5, wherein the crystal form A of compound 1 has a differential scanning calorimetry curve as shown in FIG. 2;

or, the crystal form A of compound 1 has a thermogravimetric analysis curve as shown in FIG. 3.

7. A method for the treatment of a condition related to abnormal level of uric acid in a subject in need thereof, comprising administering an effective amount of the crystal form A of compound 1 as defined in claim 1 to the subject, wherein the condition is hyperuricemia, gouty arthritis, nephrolithiasis, urinary calculus or hypertension.

* * * * *